(12) United States Patent
McGuckin, Jr. et al.

(10) Patent No.: US 8,100,936 B2
(45) Date of Patent: *Jan. 24, 2012

(54) VEIN FILTER

(75) Inventors: James F. McGuckin, Jr., Radnor, PA (US); John H. Thinnes, Philadelphia, PA (US)

(73) Assignee: Rex Medical, L.P., Conshohocken, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/791,408

(22) Filed: Jun. 1, 2010

(65) Prior Publication Data

US 2010/0312270 A1 Dec. 9, 2010

Related U.S. Application Data

(63) Continuation of application No. 11/809,561, filed on Jun. 1, 2007, which is a continuation of application No. 10/805,796, filed on Mar. 22, 2004, now Pat. No. 7,338,512.

(60) Provisional application No. 60/538,379, filed on Jan. 22, 2004.

(51) Int. Cl.
*A61F 2/01* (2006.01)

(52) U.S. Cl. ...................................... 606/200

(58) Field of Classification Search .............. 606/108, 606/191–200; 623/1.11, 23.72
See application file for complete search history.

(56) References Cited

U.S. PATENT DOCUMENTS

| | | |
|---|---|---|
| 3,744,492 A | 7/1973 | Leibinsohn |
| 3,952,747 A | 4/1976 | Kimmell, Jr. |
| 4,266,815 A | 5/1981 | Cross |
| 4,425,908 A | 1/1984 | Simon |
| 4,494,531 A | 1/1985 | Gianturco |
| 4,512,338 A | 4/1985 | Balko et al. |
| 4,619,246 A | 10/1986 | Molgaard-Nielsen et al. |
| 4,643,184 A | 2/1987 | Mobin-Uddin |
| 4,688,553 A | 8/1987 | Metals |
| 4,727,873 A | 3/1988 | Mobin-Uddin |
| 4,781,177 A | 11/1988 | Lebigot |
| 4,793,348 A * | 12/1988 | Palmaz ......................... 606/194 |
| 4,817,600 A | 4/1989 | Herms et al. |
| 4,832,055 A | 5/1989 | Palestrant |
| 4,957,501 A | 9/1990 | Lahille et al. |

(Continued)

FOREIGN PATENT DOCUMENTS

DE 3429850 2/1986

(Continued)

OTHER PUBLICATIONS

B. Braun Medical, Inc. Vena Tech™ Vena Cava Filters, Feb. 2000.

(Continued)

*Primary Examiner* — Kathleen Sonnett

(74) *Attorney, Agent, or Firm* — Neil D. Greshon

(57) ABSTRACT

A vessel filter comprising a first region and a second region wherein the filter is movable between a collapsed position for delivery to the vessel and an expanded position for placement within the vessel. A first region has a filter portion having a converging region at a first end portion to direct particles toward the center of the filter and the second region is flared in the expanded position to have a transverse dimension increasing toward a second end portion opposite the first end portion. The second region includes a vessel engaging portion at the second end portion. The second region includes a plurality of spaced apart struts with adjacent struts being joined.

18 Claims, 24 Drawing Sheets

U.S. PATENT DOCUMENTS

| | | |
|---|---|---|
| 4,990,156 A | 2/1991 | Lefebvre |
| 4,994,069 A | 2/1991 | Ritchart et al. |
| 5,059,205 A | 10/1991 | El-Nounou et al. |
| 5,133,733 A | 7/1992 | Rasmussen et al. |
| 5,152,777 A | 10/1992 | Goldberg et al. |
| 5,234,458 A | 8/1993 | Metais |
| 5,300,086 A | 4/1994 | Gory et al. |
| 5,324,304 A | 6/1994 | Rasmussen |
| 5,344,427 A | 9/1994 | Cottenceau et al. |
| 5,350,398 A | 9/1994 | Pavcnik et al. |
| 5,370,657 A * | 12/1994 | Irie .................. 606/200 |
| 5,375,612 A | 12/1994 | Cottenceau et al. |
| 5,382,261 A | 1/1995 | Palmaz |
| 5,383,887 A | 1/1995 | Nadal |
| 5,405,377 A | 4/1995 | Cragg |
| 5,531,788 A | 7/1996 | Dibie et al. |
| 5,591,197 A | 1/1997 | Orth et al. |
| 5,601,595 A | 2/1997 | Smith |
| 5,626,605 A | 5/1997 | Irie et al. |
| 5,634,942 A | 6/1997 | Chevillon et al. |
| 5,681,347 A | 10/1997 | Cathcart et al. |
| 5,683,411 A | 11/1997 | Kavteladze et al. |
| 5,690,671 A | 11/1997 | McGurk et al. |
| 5,709,704 A | 1/1998 | Nott et al. |
| 5,725,552 A | 3/1998 | Kotula et al. |
| 5,733,294 A | 3/1998 | Forber et al. |
| 5,733,329 A | 3/1998 | Wallace et al. |
| 5,746,767 A | 5/1998 | Smith |
| 5,755,779 A | 5/1998 | Horiguchi |
| 5,755,790 A | 5/1998 | Chevillon et al. |
| 5,776,162 A | 7/1998 | Kleshinski |
| 5,782,748 A | 7/1998 | Palmer et al. |
| 5,795,322 A | 8/1998 | Boudewijn |
| 5,800,457 A * | 9/1998 | Gelbfish .................. 606/200 |
| 5,810,874 A | 9/1998 | Lefebvre |
| 5,836,968 A | 11/1998 | Simon et al. |
| 5,853,420 A | 12/1998 | Chevillon et al. |
| 5,893,869 A | 4/1999 | Barnhart et al. |
| 5,895,398 A | 4/1999 | Wensel et al. |
| 5,895,410 A | 4/1999 | Forber et al. |
| 5,911,717 A | 6/1999 | Jacobsen et al. |
| 5,968,071 A | 10/1999 | Chevillon et al. |
| 5,976,172 A | 11/1999 | Homsma et al. |
| 5,984,947 A | 11/1999 | Smith et al. |
| 6,007,558 A | 12/1999 | Ravenscroft et al. |
| 6,013,093 A | 1/2000 | Nott et al. |
| 6,036,702 A | 3/2000 | Bachinski et al. |
| 6,042,598 A | 3/2000 | Tsugita et al. |
| 6,059,825 A | 5/2000 | Hobbs et al. |
| 6,063,113 A | 5/2000 | Kavteladze et al. |
| 6,066,158 A | 5/2000 | Engelson et al. |
| 6,080,178 A | 6/2000 | Meglin |
| 6,093,196 A | 7/2000 | Okada |
| 6,093,199 A | 7/2000 | Brown et al. |
| 6,096,052 A | 8/2000 | Callister et al. |
| 6,099,549 A | 8/2000 | Bosma et al. |
| 6,117,154 A | 9/2000 | Barbut et al. |
| 6,123,715 A | 9/2000 | Amplatz |
| 6,126,673 A | 10/2000 | Kim et al. |
| 6,146,404 A | 11/2000 | Kim et al. |
| 6,152,946 A | 11/2000 | Broome et al. |
| 6,165,179 A | 12/2000 | Cathcart et al. |
| 6,165,198 A | 12/2000 | McGurk et al. |
| 6,168,579 B1 | 1/2001 | Tsugita |
| 6,168,603 B1 | 1/2001 | Leslie et al. |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,187,025 B1 | 2/2001 | Machek |
| 6,193,739 B1 | 2/2001 | Chevillon et al. |
| 6,214,025 B1 | 4/2001 | Thistle et al. |
| 6,217,600 B1 | 4/2001 | DiMatteo |
| 6,231,581 B1 | 5/2001 | Shank et al. |
| 6,231,589 B1 | 5/2001 | Wessman et al. |
| 6,235,044 B1 | 5/2001 | Root et al. |
| 6,235,045 B1 | 5/2001 | Barbut et al. |
| 6,241,746 B1 | 6/2001 | Bosma et al. |
| 6,245,012 B1 | 6/2001 | Kleshinski |
| 6,251,122 B1 | 6/2001 | Tsukernik |
| 6,258,026 B1 | 7/2001 | Ravenscroft et al. |
| 6,267,776 B1 | 7/2001 | O'Connell |
| 6,273,901 B1 | 8/2001 | Whitcher et al. |
| 6,280,451 B1 | 8/2001 | Bates et al. |
| 6,280,457 B1 | 8/2001 | Wallace et al. |
| 6,290,721 B1 | 9/2001 | Heath |
| 6,328,755 B1 | 12/2001 | Marshall |
| 6,331,183 B1 | 12/2001 | Suon |
| 6,331,184 B1 | 12/2001 | Abrams |
| 6,342,062 B1 | 1/2002 | Suon et al. |
| 6,342,063 B1 | 1/2002 | Devries et al. |
| 6,344,041 B1 | 2/2002 | Kupiecki et al. |
| 6,355,051 B1 | 3/2002 | Sisskind et al. |
| 6,368,338 B1 * | 4/2002 | Konya et al. .................. 606/200 |
| 6,383,205 B1 | 5/2002 | Samson et al. |
| 6,402,771 B1 | 6/2002 | Palmer et al. |
| 6,436,120 B1 | 8/2002 | Meglin |
| 6,436,121 B1 | 8/2002 | Blom |
| 6,443,971 B1 | 9/2002 | Boylan et al. |
| 6,443,972 B1 | 9/2002 | Bosma et al. |
| 6,447,530 B1 | 9/2002 | Ostrovsky et al. |
| 6,447,531 B1 | 9/2002 | Amplatz |
| 6,458,139 B1 | 10/2002 | Palmer et al. |
| 6,468,290 B1 | 10/2002 | Weldon et al. |
| 6,482,222 B1 | 11/2002 | Bruckheimer et al. |
| 6,506,205 B2 * | 1/2003 | Goldberg et al. ............. 606/200 |
| 6,517,559 B1 | 2/2003 | O'Connell |
| 6,527,962 B1 | 3/2003 | Nadal |
| 6,537,294 B1 | 3/2003 | Boyle et al. |
| 6,540,767 B1 | 4/2003 | Walak et al. |
| 6,551,342 B1 | 4/2003 | Shen et al. |
| 6,562,058 B2 | 5/2003 | Seguin et al. |
| 6,599,307 B1 | 7/2003 | Huter et al. |
| 6,605,102 B1 | 8/2003 | Mazzocchi et al. |
| 6,652,558 B2 | 11/2003 | Patel et al. |
| 6,656,202 B2 | 12/2003 | Papp et al. |
| 6,660,021 B1 | 12/2003 | Palmer et al. |
| 6,695,878 B2 | 2/2004 | McGuckin et al. |
| 6,783,538 B2 | 8/2004 | McGuckin et al. |
| 6,793,665 B2 | 9/2004 | McGuckin et al. |
| 6,890,340 B2 | 5/2005 | Duane |
| 6,932,831 B2 | 8/2005 | Forber |
| 6,958,074 B2 | 10/2005 | Russell |
| 6,972,025 B2 | 12/2005 | WasDyke |
| 6,989,021 B2 | 1/2006 | Bosma et al. |
| 6,994,092 B2 | 2/2006 | Van der Burg et al. |
| 7,037,321 B2 | 5/2006 | Sachdeva et al. |
| 7,097,651 B2 | 8/2006 | Harrison et al. |
| 7,232,462 B2 | 6/2007 | Schaeffer et al. |
| 7,279,000 B2 | 10/2007 | Cartier et al. |
| 7,316,708 B2 | 1/2008 | Gordon et al. |
| 7,534,251 B2 | 5/2009 | WasDyke |
| 7,749,246 B2 * | 7/2010 | McGuckin et al. ............ 606/200 |
| 2002/0058911 A1 | 5/2002 | Gilson et al. |
| 2002/0116024 A1 | 8/2002 | Goldberg et al. |
| 2002/0193827 A1 | 12/2002 | McGuckin et al. |
| 2002/0193828 A1 | 12/2002 | Griffin et al. |
| 2003/0130680 A1 * | 7/2003 | Russell .................. 606/200 |
| 2003/0195555 A1 | 10/2003 | Khairkhahan et al. |
| 2003/0208227 A1 | 11/2003 | Thomas |
| 2003/0208253 A1 | 11/2003 | Beyer et al. |
| 2004/0044361 A1 | 3/2004 | Frazier et al. |
| 2004/0073252 A1 | 4/2004 | Goldberg et al. |
| 2004/0093017 A1 | 5/2004 | Chanduszko |
| 2004/0186510 A1 | 9/2004 | Weaver |
| 2004/0215230 A1 | 10/2004 | Frazier et al. |
| 2004/0230220 A1 | 11/2004 | Osborne |
| 2005/0004596 A1 | 1/2005 | McGuckin et al. |
| 2005/0015111 A1 | 1/2005 | McGuckin et al. |
| 2005/0027314 A1 | 2/2005 | WasDyke |
| 2005/0043757 A1 | 2/2005 | Arad et al. |
| 2005/0165442 A1 | 7/2005 | Thinnes, Jr. et al. |
| 2005/0182439 A1 | 8/2005 | Lowe |
| 2005/0234503 A1 | 10/2005 | Ravenscroft et al. |
| 2005/0251199 A1 | 11/2005 | Osborne et al. |
| 2005/0267514 A1 | 12/2005 | Osborne et al. |
| 2005/0288704 A1 | 12/2005 | Cartier et al. |

| | | | | | | |
|---|---|---|---|---|---|---|
| 2006/0030875 | A1 | 2/2006 | Tessmer | WO | 0162184 | 8/2001 |
| 2006/0058832 | A1 | 3/2006 | Melzer et al. | WO | 0172239 | 10/2001 |
| 2006/0079928 | A1 | 4/2006 | Cartier et al. | WO | 0211812 | 2/2002 |
| 2006/0100660 | A1 | 5/2006 | Osborne et al. | WO | 03063732 | 8/2003 |
| 2006/0106417 | A1 | 5/2006 | Tessmer et al. | WO | 2004049973 | 6/2004 |
| 2006/0178695 | A1 | 8/2006 | Decant et al. | WO | 2005034764 | 4/2005 |
| 2006/0206138 | A1 | 9/2006 | Eidenschink | WO | 2005 117750 | 12/2005 |
| 2007/0005095 | A1 | 1/2007 | Osborne et al. | WO | 2006 036457 | 4/2006 |
| 2007/0032816 | A1 | 2/2007 | O'Connell et al. | WO | 20050034764 | 4/2006 |
| 2007/0173885 | A1 | 7/2007 | Cartier et al. | | | |

FOREIGN PATENT DOCUMENTS

| | | |
|---|---|---|
| EP | 1707233 | 10/2006 |
| FR | 2567405 | 1/1986 |
| WO | 9312723 | 7/1993 |
| WO | 9509567 | 4/1995 |
| WO | 9925252 | 5/1999 |
| WO | 0145590 | 6/2001 |

OTHER PUBLICATIONS

Gianturco-Roehm, Bird's Nest® Vena Cava Filter.
Cordis Corporation, TrapEase™ Permanent Vena Cava Filter, "A Small, Easy and Verstaile System for Optimal Pulmonary Emboli Prevention", 2000 (4 pages).

\* cited by examiner

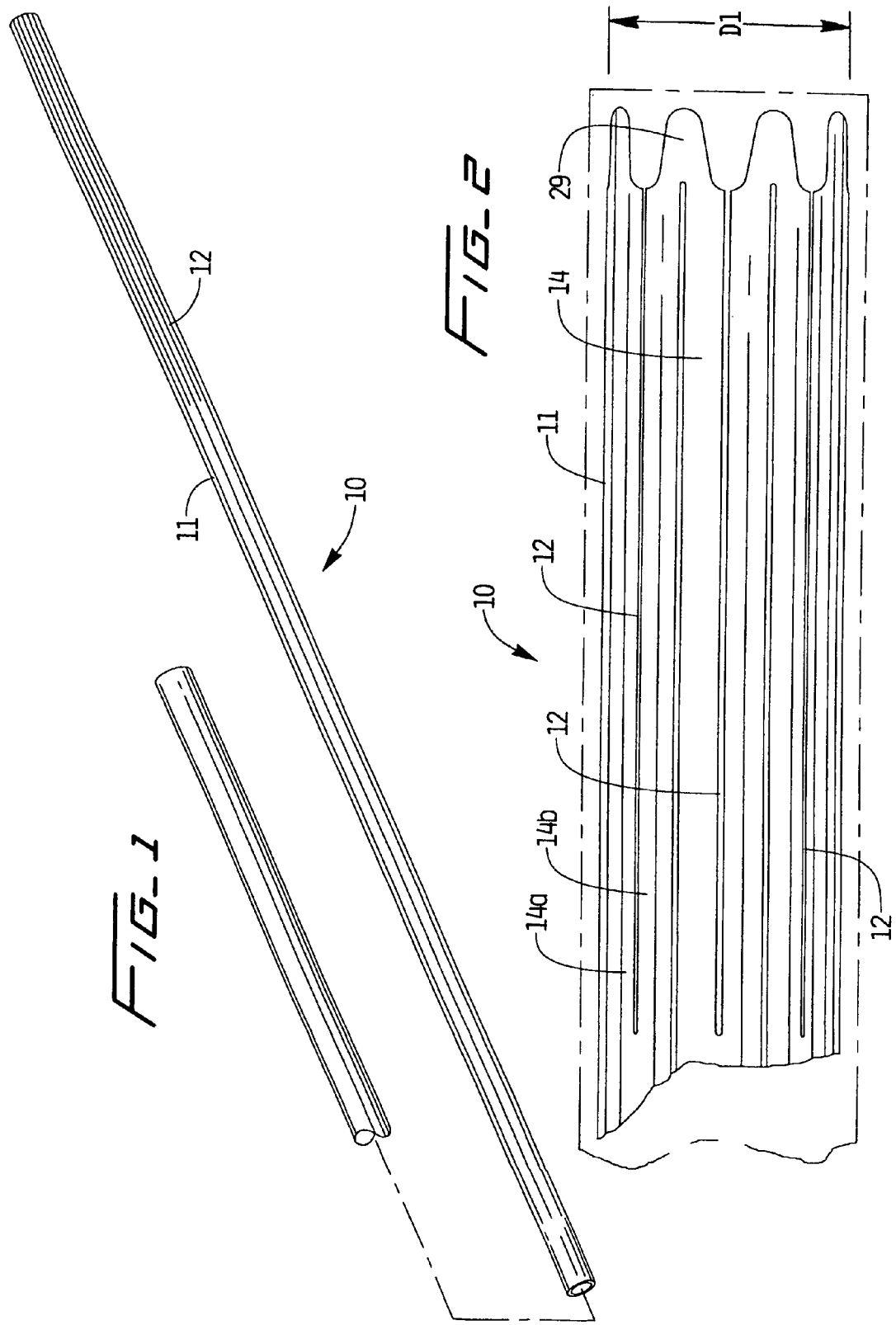

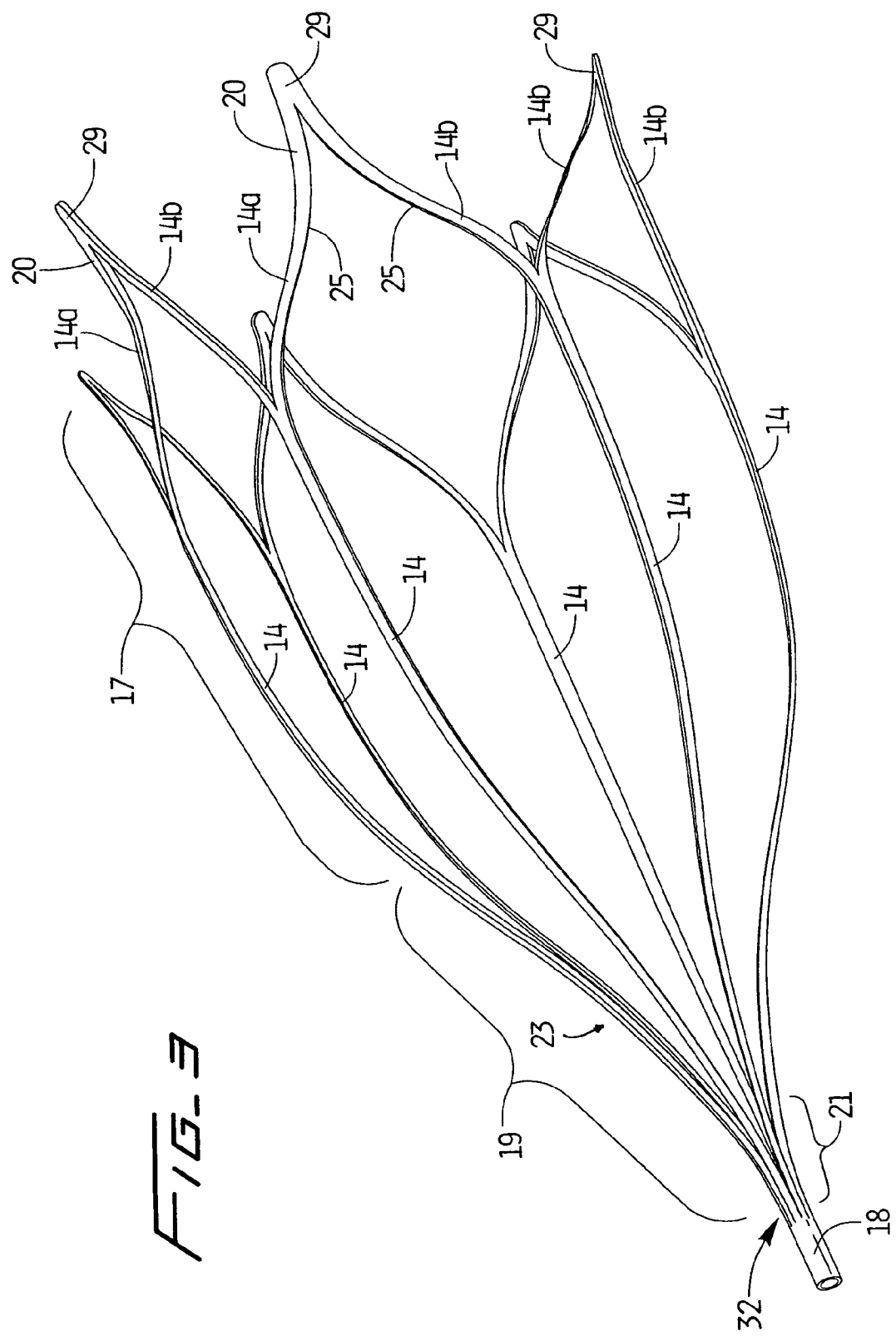

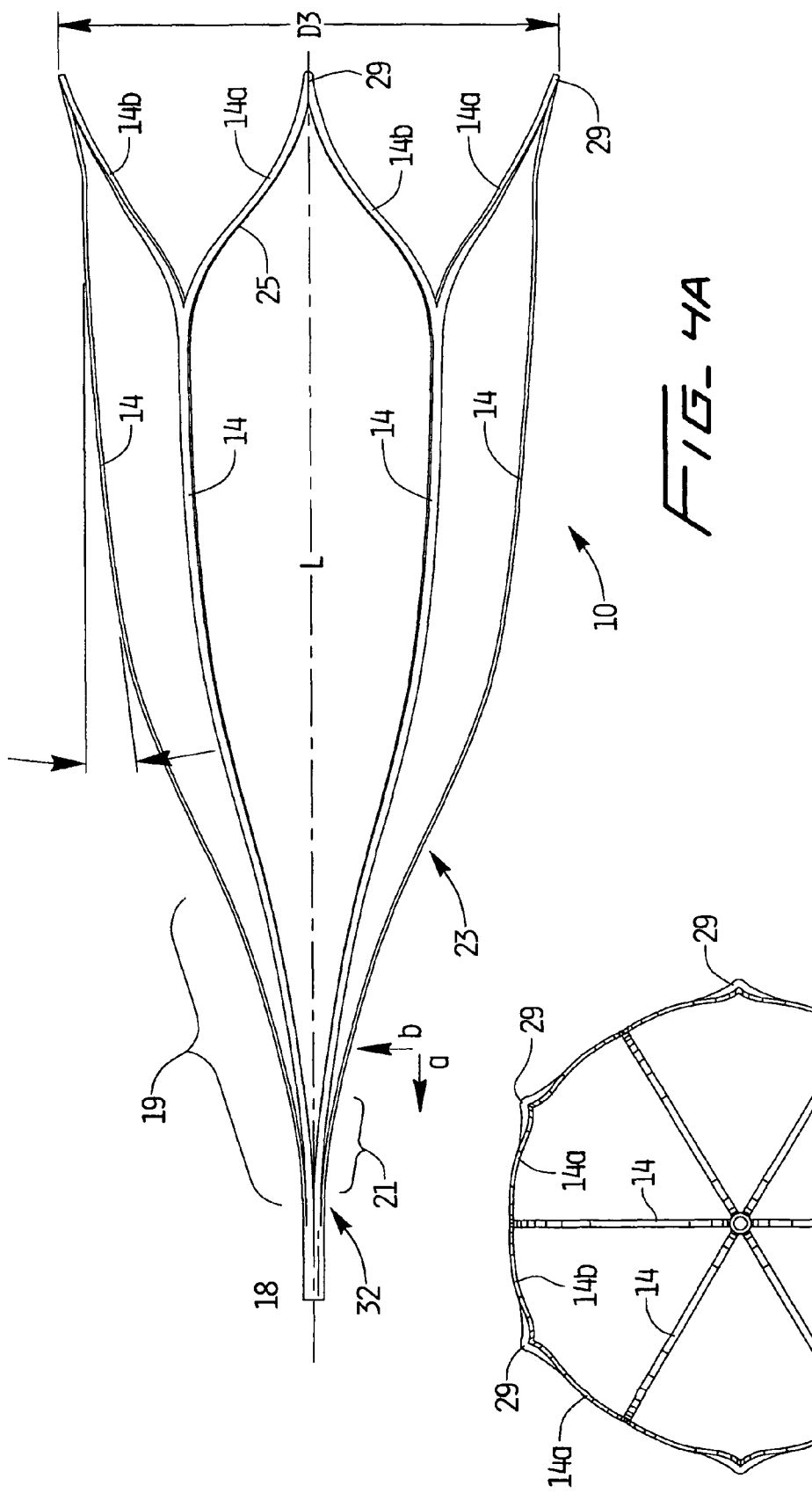

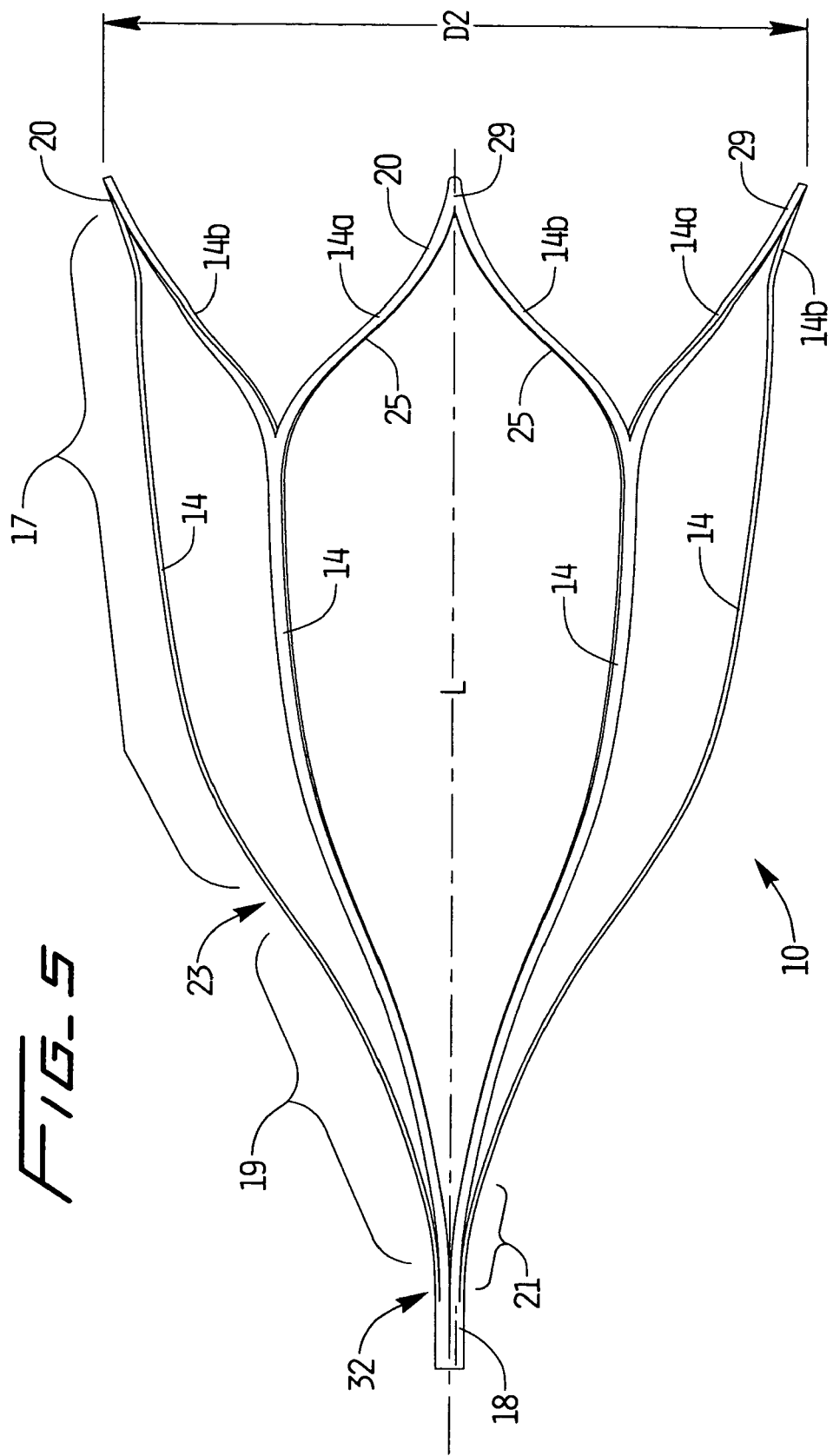

FIG_6A
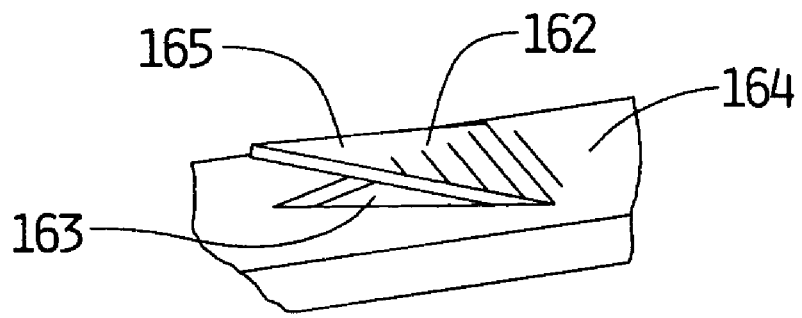
FIG_6B
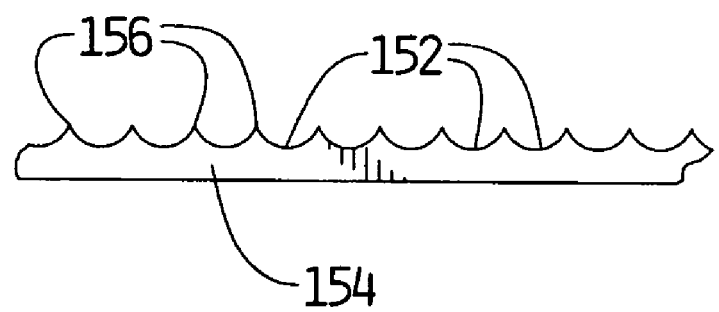

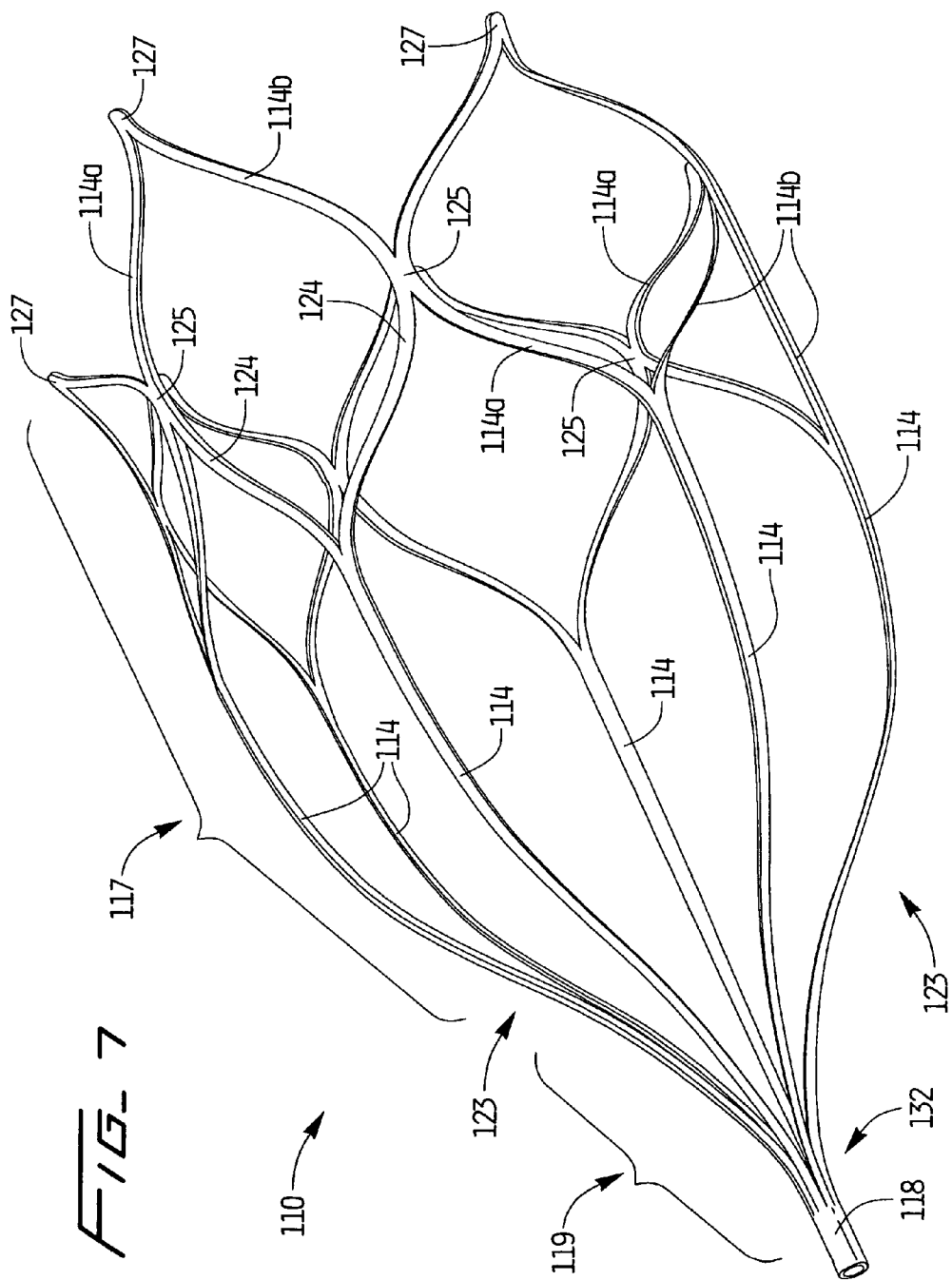

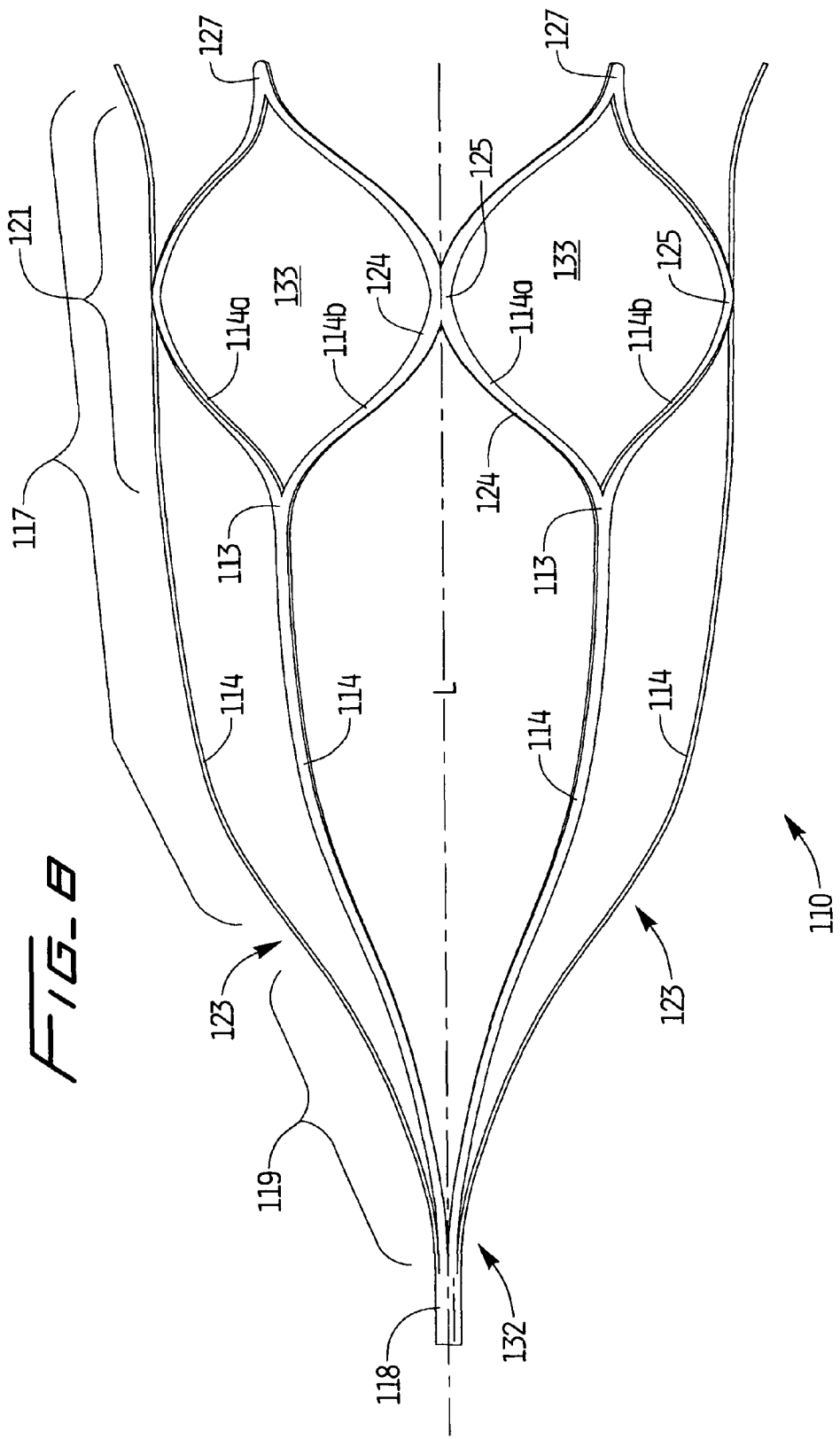

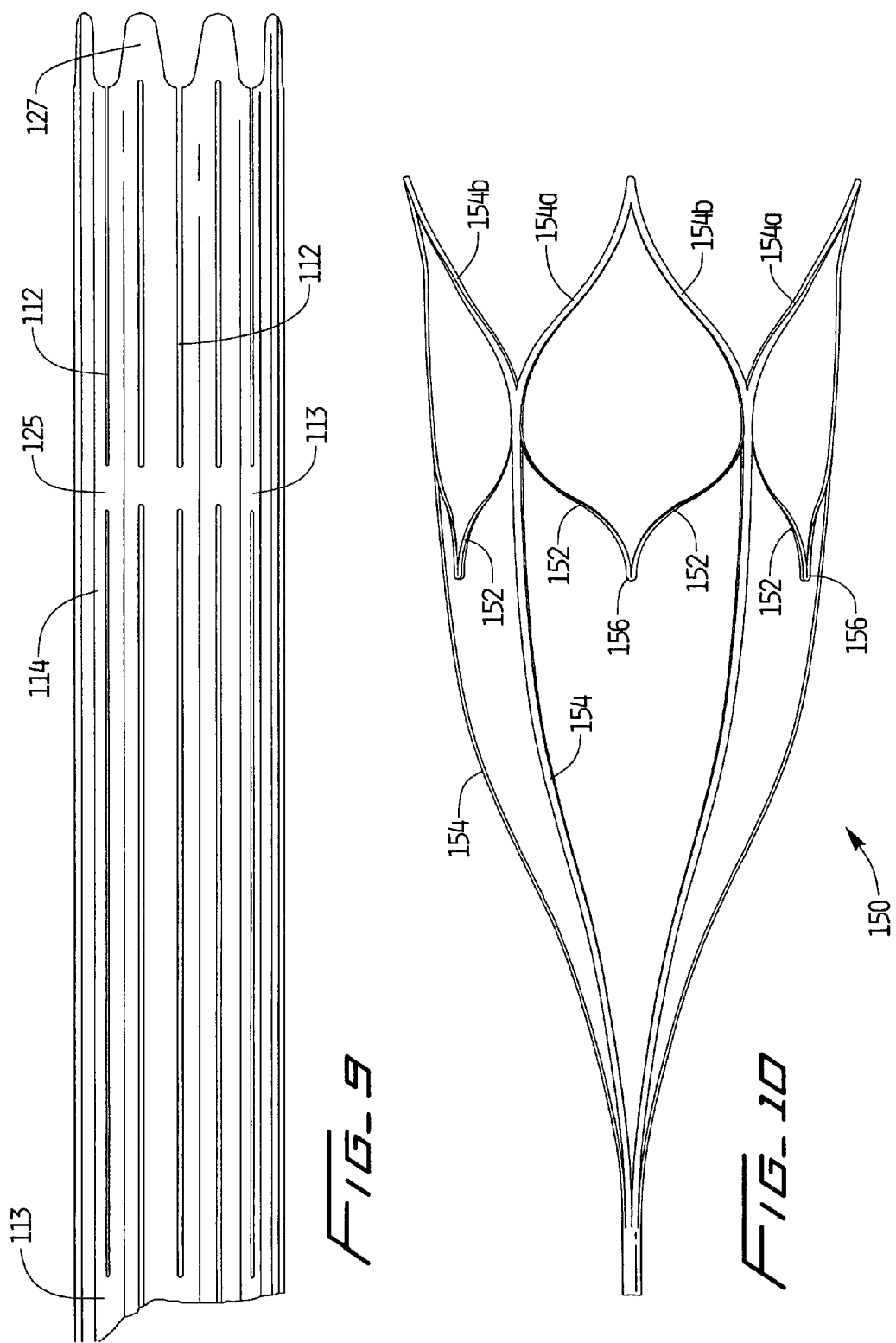

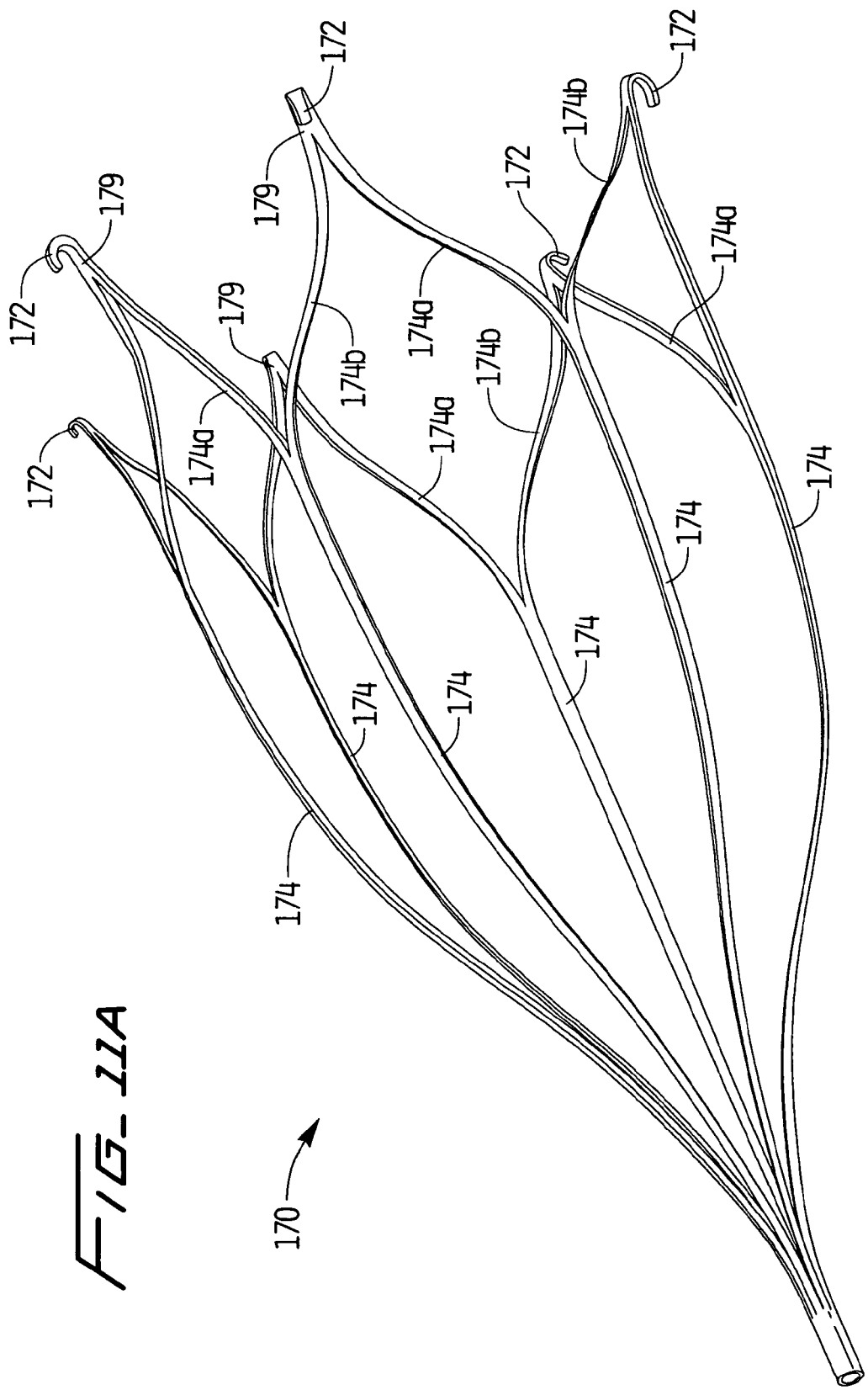

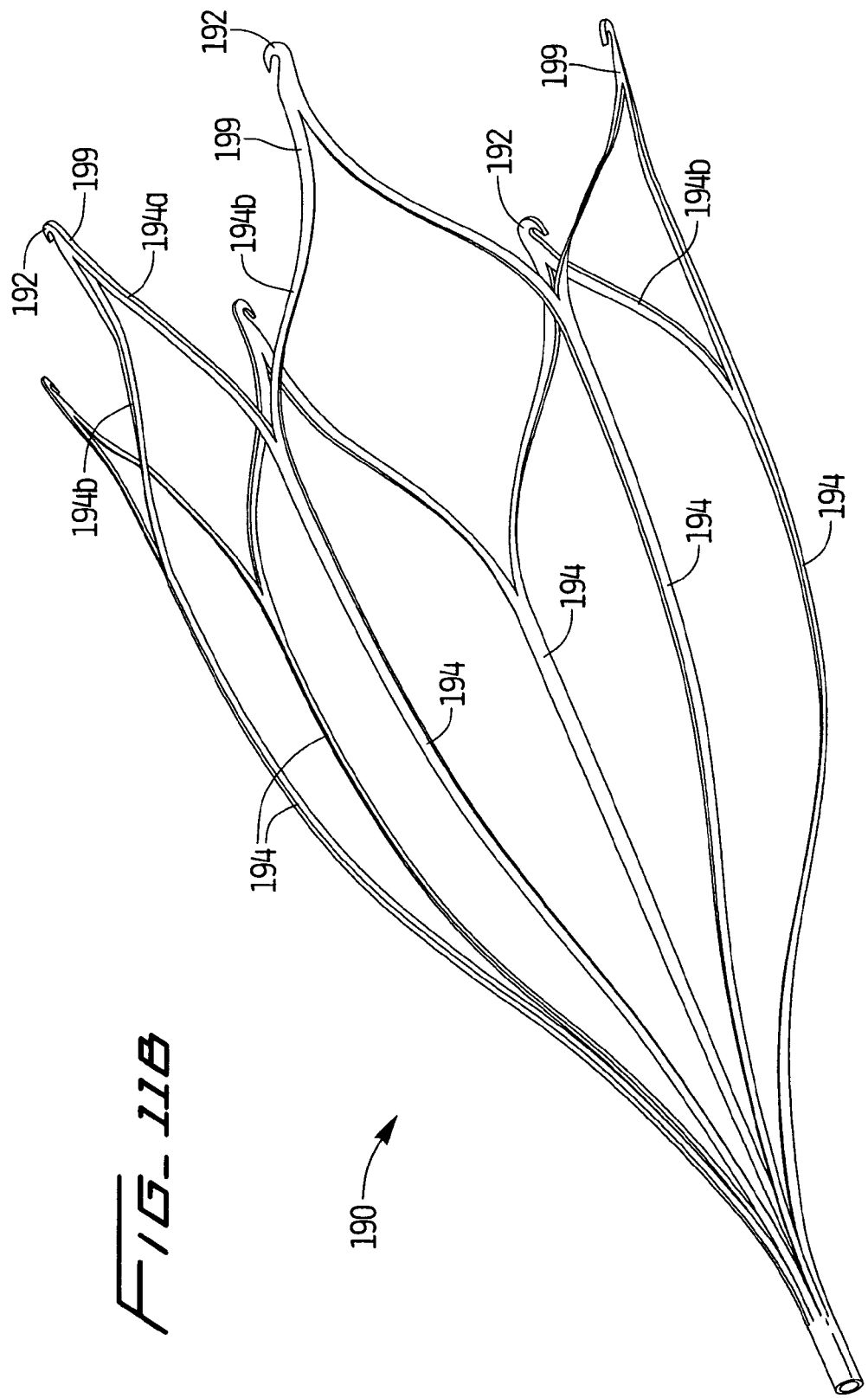

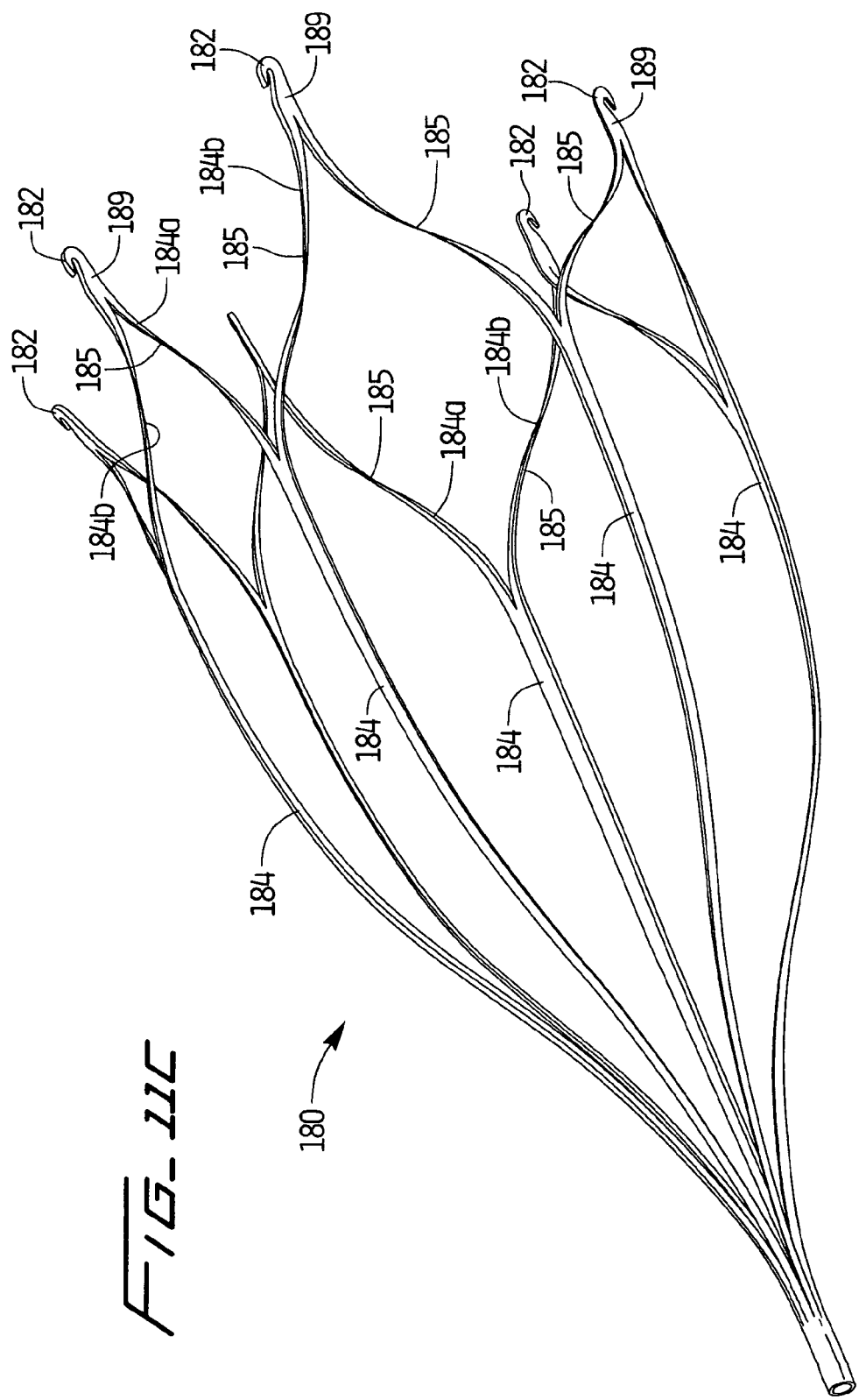

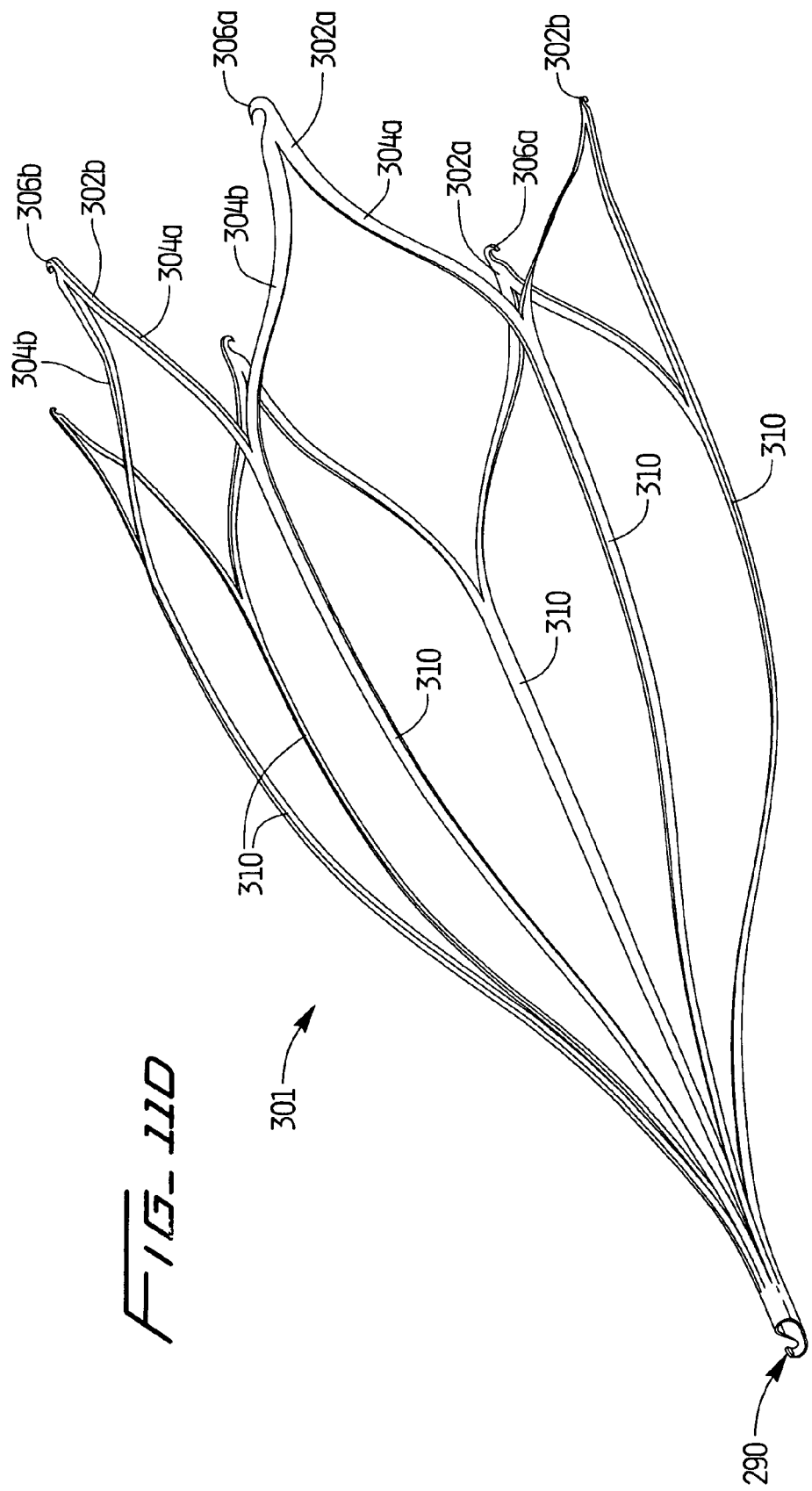

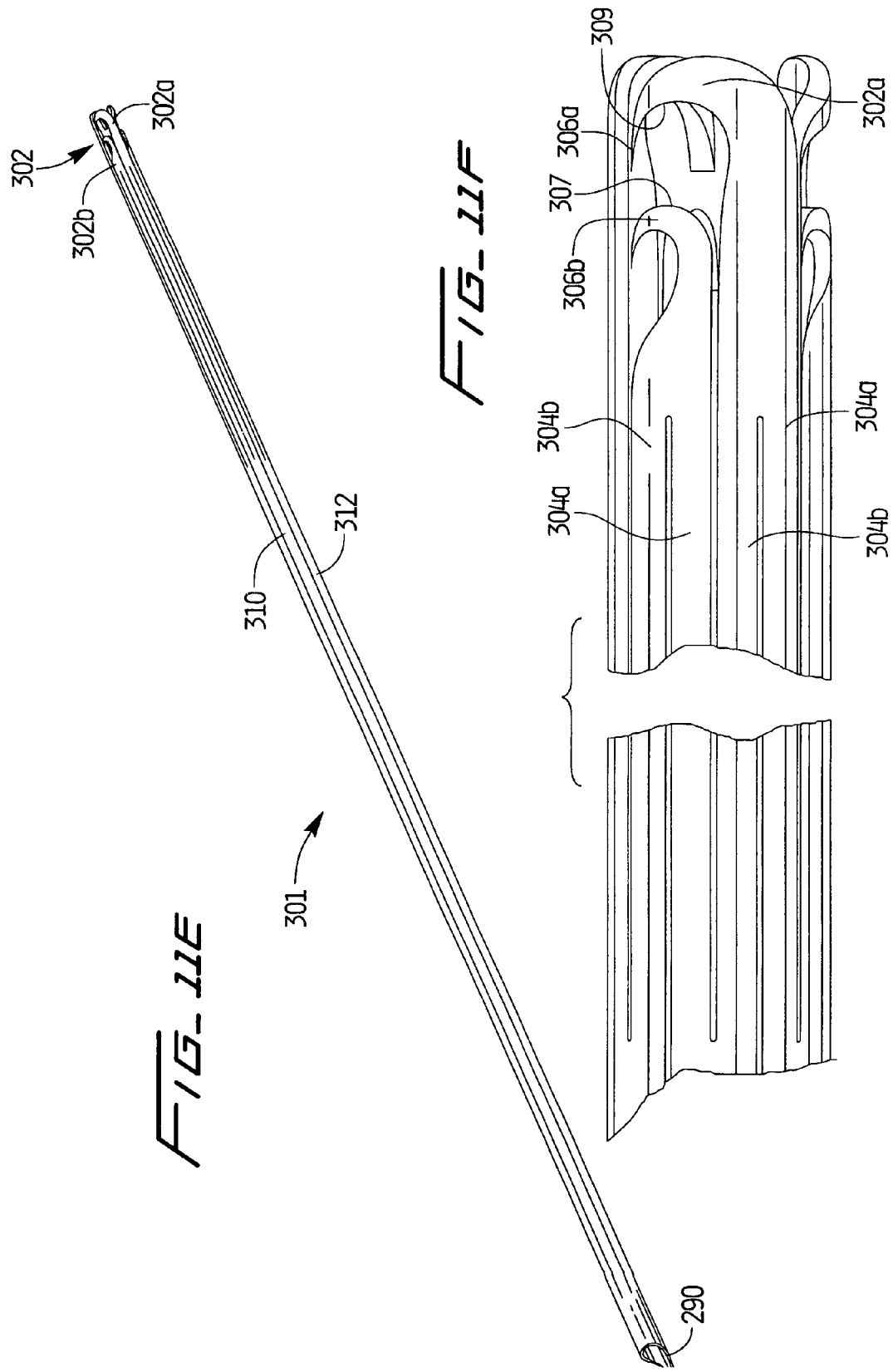

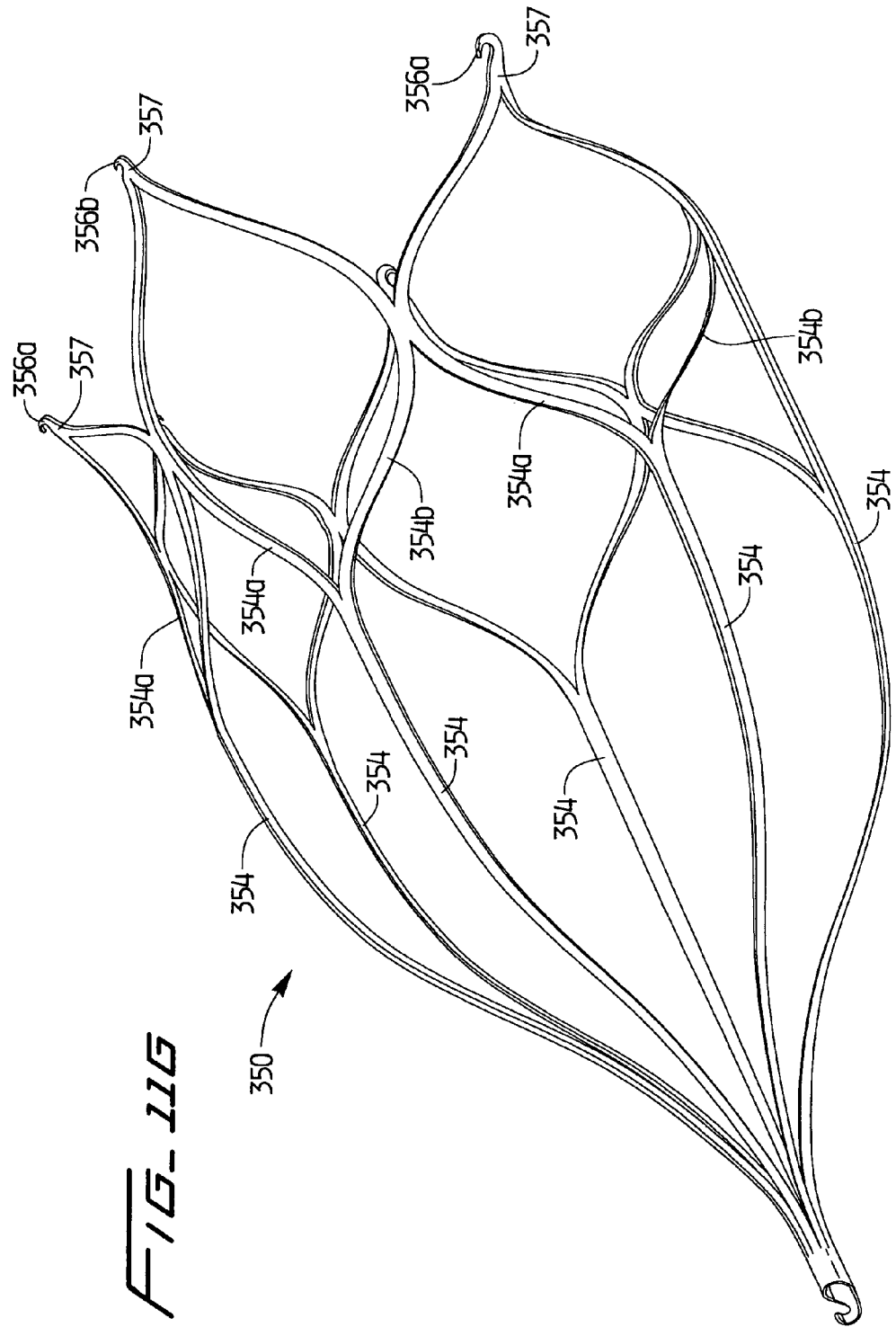

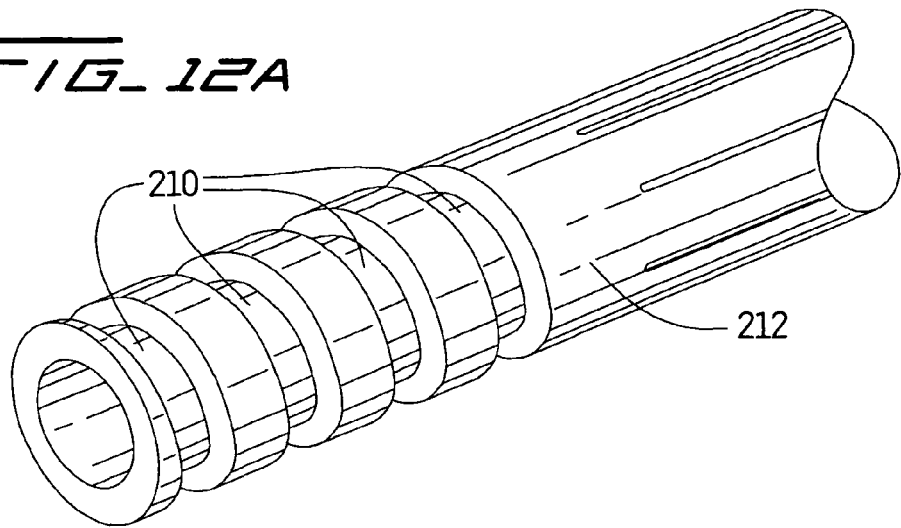
FIG_12A
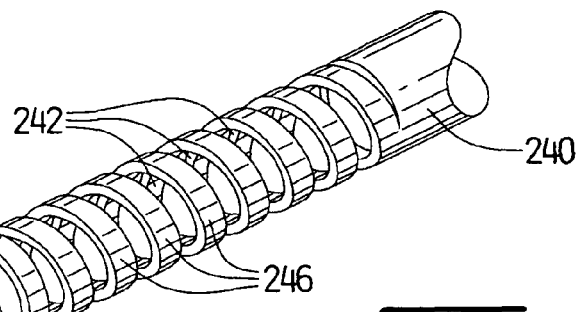
FIG_12B
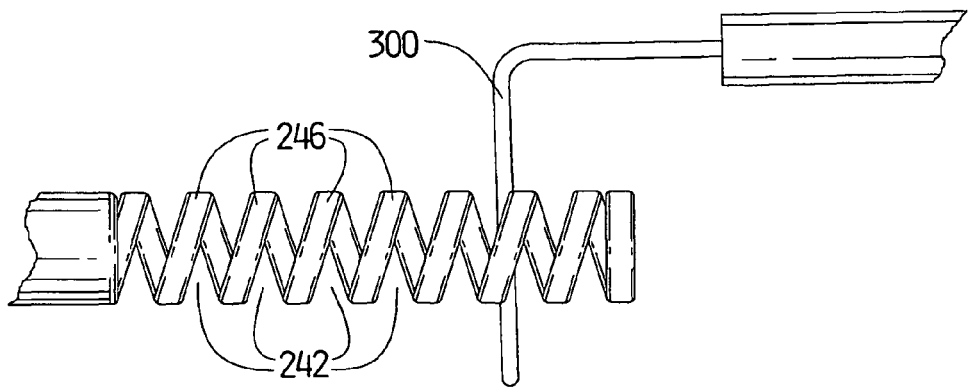
FIG_12C

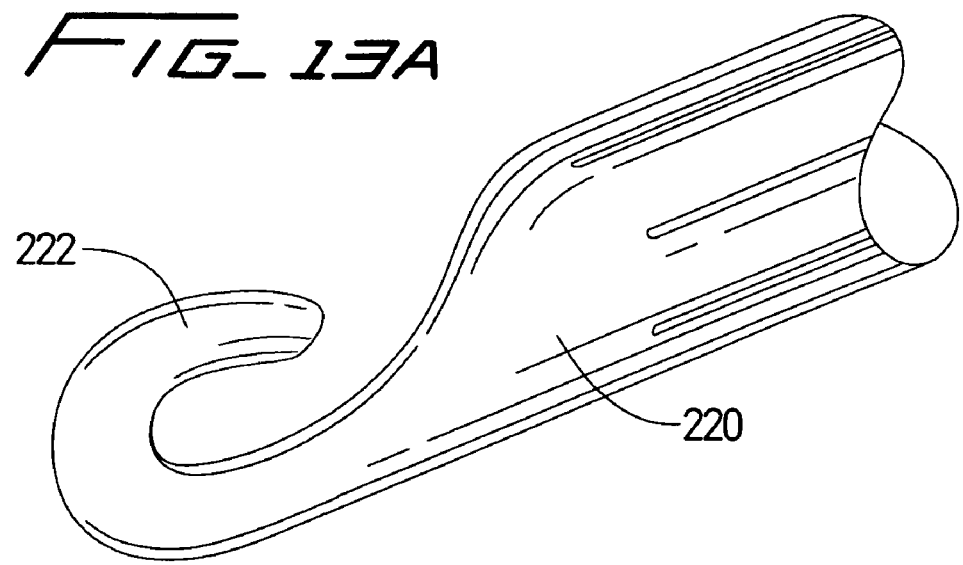
FIG_13A
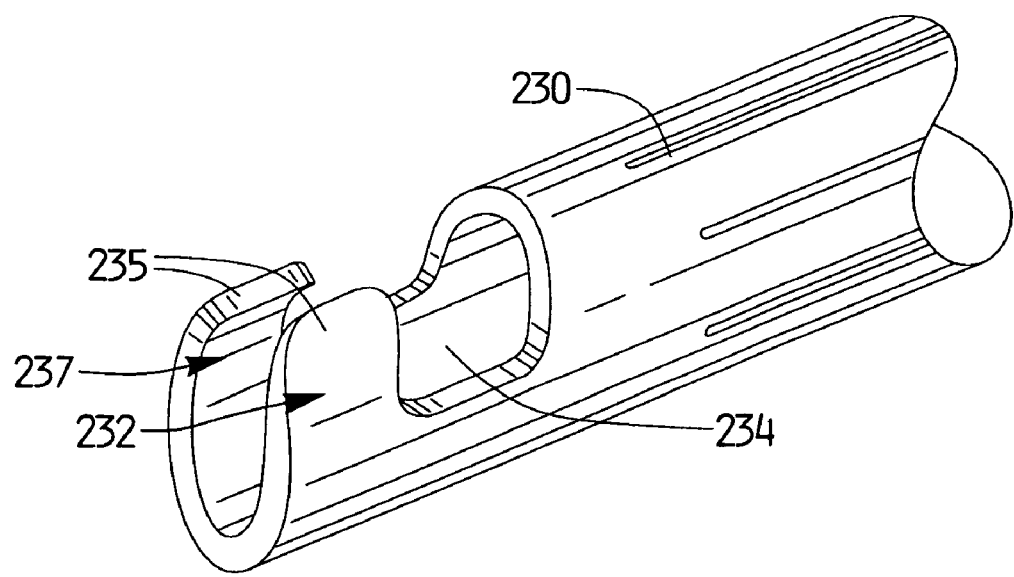
FIG_13B

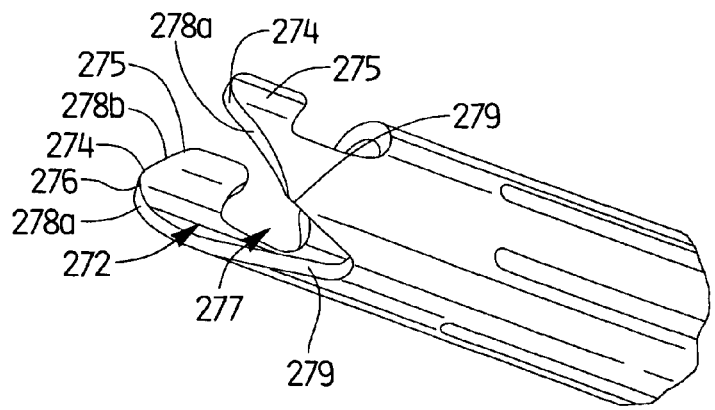
FIG_13C
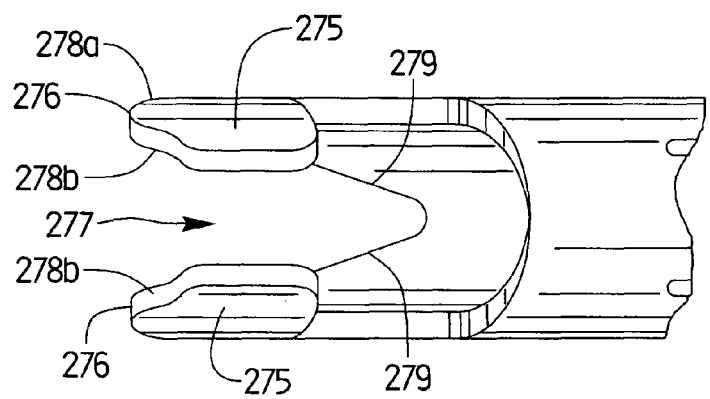
FIG_13D
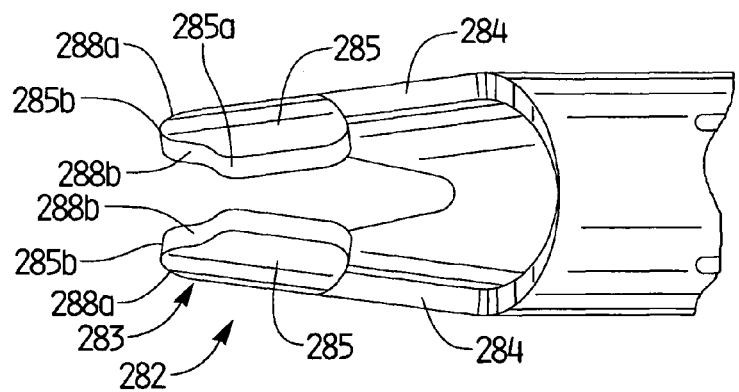
FIG_13E

FIG_13F
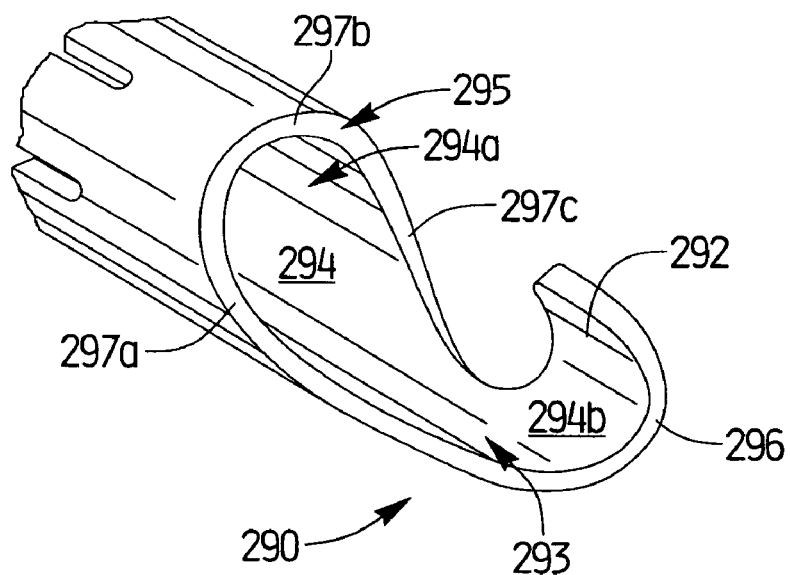
FIG_13G
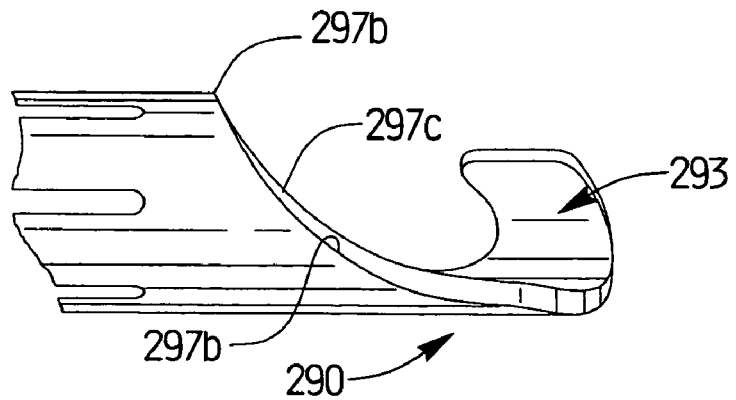

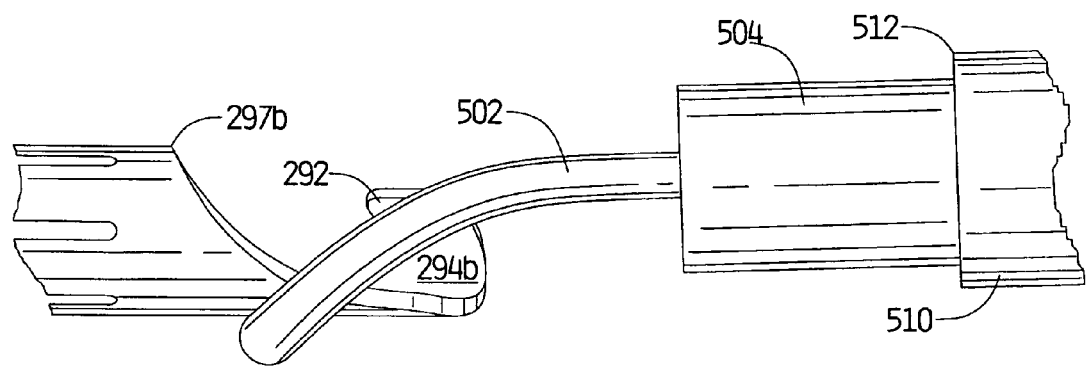
FIG_13H
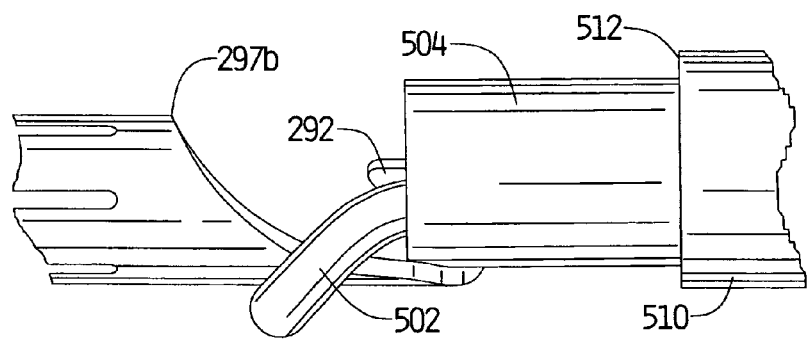
FIG_13I
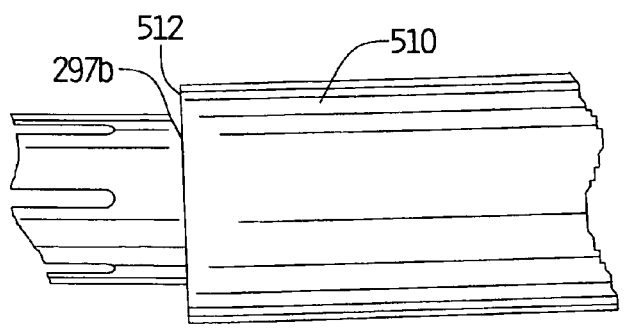
FIG_13J

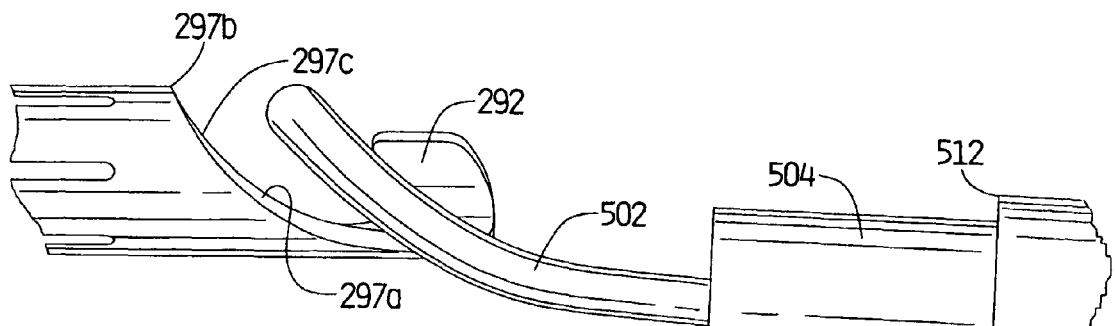
FIG_13K
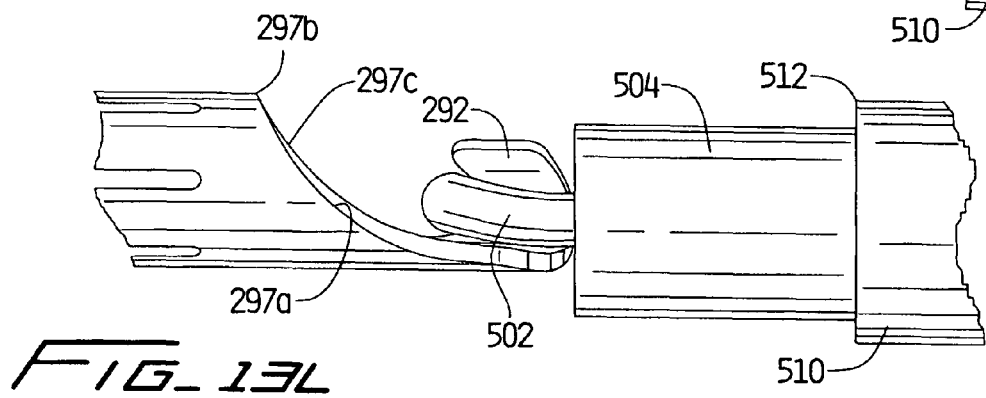
FIG_13L
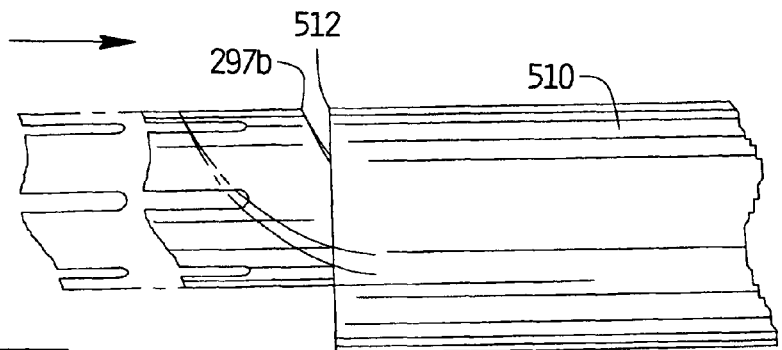
FIG_13M
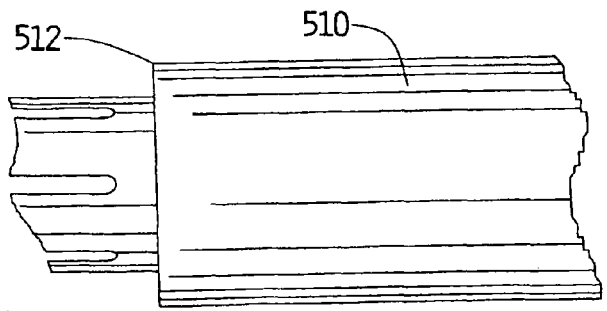
FIG_13N

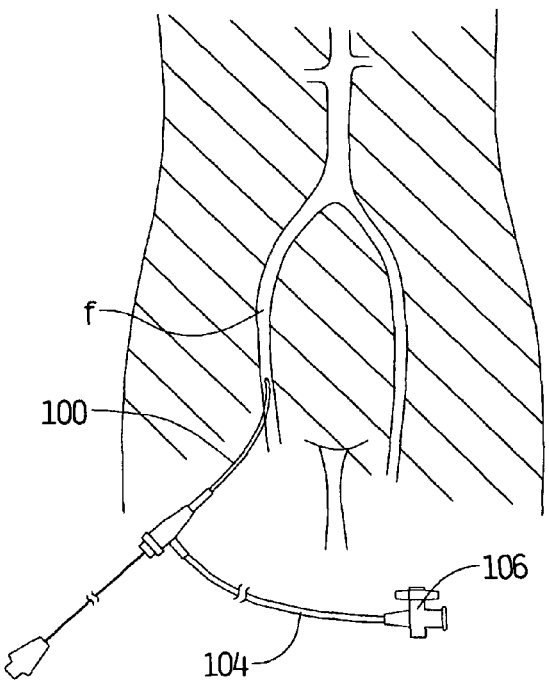
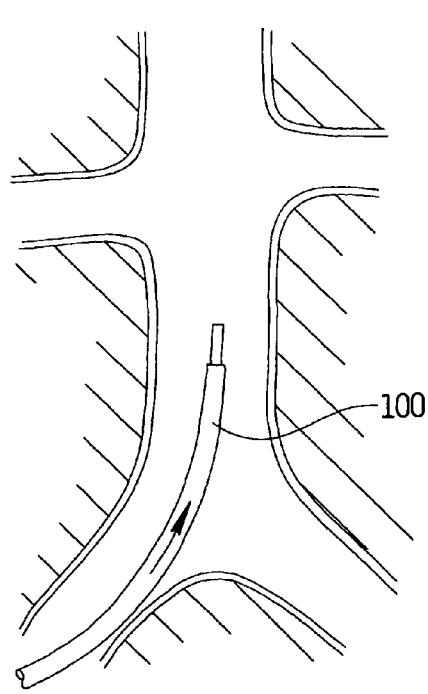
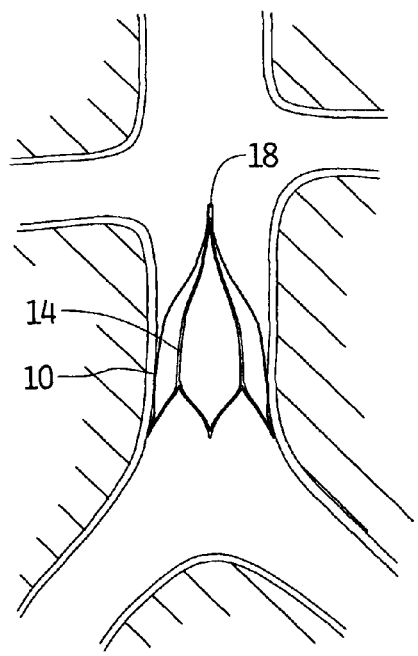

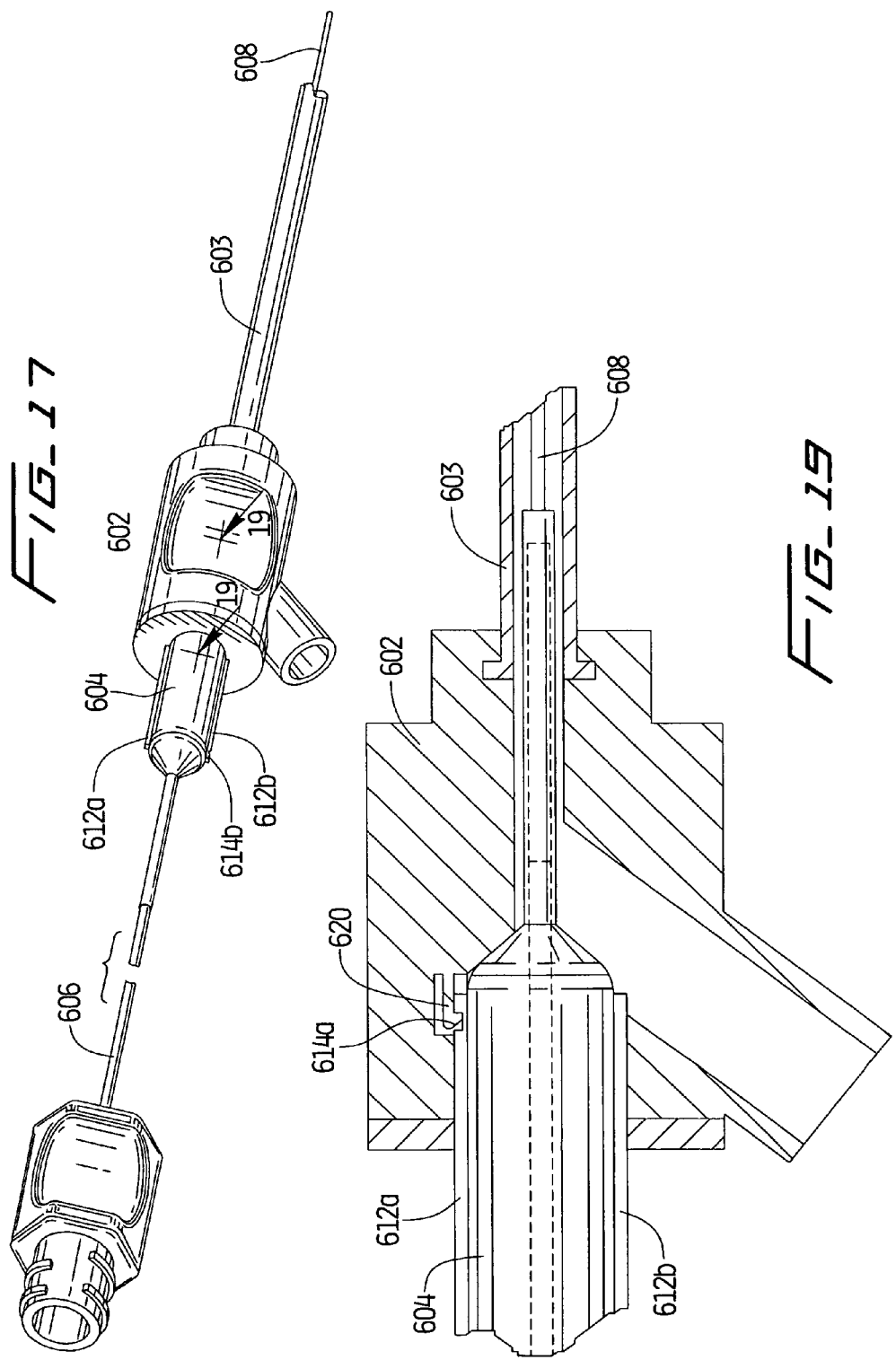

VEIN FILTER

This application is a continuation of application Ser. No. 11/809,561, filed on Jun. 1, 2007, which is a continuation of application Ser. No. 10/805,796, filed Mar. 22, 2004, now U.S. Pat. No. 7,338,512, which claims priority from provisional application Ser. No. 60/538,379, filed on Jan. 22, 2004. The entire contents of each of these applications are incorporated herein by reference.

BACKGROUND

1. Technical Field

This application relates to a vascular filter and more particularly to a vein filter for capturing blood clots within the vessel.

2. Background of Related Art

Passage of blood clots to the lungs is known as pulmonary embolism. These clots typically originate in the veins of the lower limbs and can migrate through the vascular system to the lungs where they can obstruct blood flow and therefore interfere with oxygenation of the blood. Pulmonary embolisms can also cause shock and even death.

In some instances, blood thinning medication, e.g. anticoagulants such as Heparin, or sodium warfarin can be given to the patient. These medications, however, have limited use since they may not be able to be administered to patients after surgery or stroke or given to patients with high risk of internal bleeding. Also, this medication approach is not always effective in preventing recurring blood clots.

Therefore, surgical methods to reduce the likelihood of such pulmonary embolisms by actually blocking the blood clot from reaching the lungs have been developed. One surgical method of treatment involved major surgery where the size of the vessel lumen was restricted by placement of ligatures or clips around the vein, e.g. the inferior vena cava which transports blood from the lower portion of the body to the heart and lungs. This prevented passage of dangerously large blood clots through the vein to the lungs. However, this approach is an invasive surgical procedure, requiring an abdominal incision and general anesthesia and frequently causing vessel thrombosis and lower extremity swelling. Also, there is a lengthy patient recovery time and additional hospital and surgeon expenses associated with this major surgery. In fact, oftentimes, the patients requiring the surgery are unhealthy and the major surgery and general anesthesia poses a risk in and of itself.

To avoid such invasive surgery, less invasive surgical techniques have been developed. These involve the placement of a mechanical barrier in the inferior vena cava. These barriers are in the form of filters and are typically inserted through either the femoral vein in the patient's leg or the right jugular vein in the patient's neck or arm under local anesthesia. The filters are then advanced intravascularly to the inferior vena cava where they are expanded to block migration of the blood clots from the lower portion of the body to the heart and lungs.

These prior filters take various forms. One type of filter is composed of coiled wires such as disclosed in U.S. Pat. Nos. 5,893,869 and 6,059,825. Another type of filter consists of legs with free ends having anchors for embedding in the vessel wall to hold the filter. These filters are disclosed, for example, in U.S. Pat. Nos. 4,688,553, 4,781,173, 4,832,055, and 5,059,205, 5,984,947 and 6,007,558. Another type of filter is disclosed in U.S. Pat. No. 6,214,025 consisting of wires twisted together to form a cylindrical anchoring portion conforming to the inner vessel wall surface to exert a radial force and a conical filtering portion.

Several factors have to be considered in designing vein filters. One factor is that the filter needs to be securely anchored within the vessel wall, while avoiding traumatic engagement and damage to the wall as well as damage to the neighboring abdominal aorta. Another factor is that the filter must be collapsible to a sufficiently small size to be easily maneuvered and atraumatically advanced intravascularly to the inferior vena cava or other target vessel. Thirdly, the filter should direct the blood clots to the center of the vessel to improve dissolution of the clot within the vessel by the blood flow.

It would be advantageous to provide a vein filter that satisfies the foregoing parameters. Namely, such vein filter would advantageously have sufficient anchoring force to retain the filter within the vessel while providing atraumatic contact with the vessel wall, would have a minimized insertion (collapsed) profile to facilitate delivery through the vascular system to the surgical site, and would enable migration of the captured blood clots to the center of the vessel. Moreover, it would also be advantageous to provide a filter that could simplify insertion through the femoral or the right jugular vein or arm into the inferior vena cava.

Additionally, the need for a vein filter in many patients is temporary. In these instances it would be advantageous to provide a vein filter that satisfies the foregoing factors and in addition could be readily removed from the patient. Thus, the filter would advantageously have structure to provide sufficient anchoring while enabling atraumatic removal from the vessel. It would further be advantageous if the filter could be removed minimally invasively, e.g. intravascularly.

Filters that are temporary are typically removed by a retrieval snare which pulls the filter into a retrieval sheath. It would be advantageous to provide a filter which facilitates grasping by the snare as well as facilitates withdrawal by providing a smooth transition into a retrieval sheath.

SUMMARY

The present invention overcomes the problems and deficiencies of the prior art. The present invention provides a vessel filter movable between a collapsed position for delivery to the vessel and an expanded position for placement within the vessel. A first region of the filter has a filter portion having a converging region at a first end portion to direct particles toward the center of the filter and the second region is flared in the expanded position to have a transverse dimension increasing toward a second end portion opposite the first end portion. The second region includes a vessel engaging portion at the second end portion, and includes a plurality of spaced apart struts with adjacent struts being joined.

The filter is preferably formed from a laser cut tube and composed of shape memory material. Preferably, the adjacent struts are joined by two connecting struts with each of the two connecting struts extending inwardly toward the other connecting strut to form a substantially V-shaped configuration.

The vessel filter can include a plurality of vessel engaging members with pointed ends extending from the struts to engage the vessel wall to increase retention. In one embodiment, one or more of the plurality of spaced apart struts terminates in vessel engaging hooks.

The filter can include the plurality of spaced apart struts dividing at an end portion to form two connecting struts which extend away from each other, wherein each connecting strut extends toward a connecting strut of an adjacent strut. In one embodiment, the connecting strut of adjacent struts are joined at an intermediate region and further extend away from each other to join the connecting strut emanating from the same strut. In one embodiment, the connecting struts form a closed oval like region.

In one embodiment, the filter includes at the first end portion multiple recesses axially spaced from one another and configured to receive a removing instrument to remove the filter.

The present invention also provides a vessel filter comprising a first region and a second region and movable between a collapsed position for delivery to the vessel and an expanded position for placement within the vessel. The filter is substantially bell-shaped in the expanded position. The first region of the filter has a filter portion having a converging region at a first end portion and the second region has a mounting portion for mounting the vessel filter within the vessel. The mounting portion includes a flared region. The second region includes a plurality of struts extending from the filter portion and dividing into oppositely directed struts at a first end and then converging with an oppositely directed strut of an adjacent strut.

The mounting portion can include vessel engaging members to enhance retention of the filter. In one embodiment, one or more of the plurality of struts terminates in vessel engaging hooks.

In one embodiment, oppositely directed struts emanating from the strut are rejoined to each other at a second end.

In another aspect of the present invention, a vessel filter is provided comprising a first region including a filtering section for capturing particles and having a first transverse dimension and a second region including a mounting section for mounting the filter within the vessel. The mounting section has a second transverse dimension greater than the first transverse dimension and includes vessel engaging structure to retain the filter. The first region further includes a plurality of cutouts configured to receive a removal tool such as a retrieval snare to remove the filter from the vessel, the cutouts being axially spaced. In one embodiment the cutouts are helically formed.

The present invention also provides a vessel filter comprising a first region including a filtering section for capturing particles and having a first transverse dimension and a second region including a mounting section for mounting the filter within the vessel. The mounting section has a second transverse dimension greater than the first transverse dimension and includes vessel engaging structure to retain the filter. The first region further includes a retrieval region including a hook having a cutout exposing an internal annular surface dimensioned to receive a portion of a snare sheath.

Preferably, the retrieval region includes a radiused region having first and second curved surfaces extending distally and inwardly.

The present invention also provides a vessel filter comprising a first region and a second region. The first region includes a filtering section for capturing particles and having a first transverse dimension and the second region includes a mounting section for mounting the filter within the vessel. The mounting section has a second transverse dimension greater than the first transverse dimension and includes vessel engaging structure to retain the filter. The first region further includes a retrieval region including a hook at a proximal end thereof and a curved wall spaced axially from the hook to provide a camming surface to facilitate entry into a retrieval sheath.

The present invention also provides a vessel filter comprising a first region including a filtering section for capturing particles and having a first transverse dimension and a second region including a mounting section for mounting the filter within the vessel. The mounting section has a second transverse dimension greater than the first transverse dimension and includes vessel engaging structure to retain the filter. The vessel engaging structure includes a first set of hooks and a second set of hooks, wherein each set of hooks is positioned at an end of the mounting section. The first set of hooks has a transverse dimension greater than a transverse dimension of the second set of hooks.

Preferably, the mounting section includes a plurality of struts and one of the hooks extends from each of the struts. Preferably, an end portion of each strut defines a plane and each hook extending from the strut lies in the plane of the strut. In a preferred embodiment, the first set of struts is axially offset from the second set of struts. In a preferred embodiment the filter is formed from a laser cut tube, cut to form a set of struts, wherein each of the hooks of the second set of hooks is formed of a transverse dimension substantially corresponding to a dimension of one strut and each of the hooks of the first set is formed of a transverse dimension substantially corresponding to a dimension of two adjacent struts.

BRIEF DESCRIPTION OF THE DRAWINGS

Preferred embodiment(s) of the present disclosure are described herein with reference to the drawings wherein:

FIG. 1 is a perspective view of a first embodiment of the vein filter of the present invention in the collapsed configuration;

FIG. 2 is an enlarged side view of a portion of the vein filter of FIG. 1;

FIG. 3 is a perspective view of the vein filter of FIG. 1 in an expanded configuration;

FIG. 4A is a side view of the vein filter of FIG. 1 in another expanded configuration;

FIG. 4B is a front view of the vein filter of FIG. 4 in the expanded configuration;

FIG. 5 is a side view of the vein filter of FIG. 3 in the expanded configuration;

FIG. 6A is a close up view of a portion of the struts showing one embodiment of anchoring elements having pointed ends;

FIG. 6B is a close up view of a portion of one of the struts showing another embodiment of anchoring elements in the form of hemispherical cutouts;

FIG. 7 is a perspective view of an alternate embodiment of the vein filter of the present invention shown in the expanded configuration;

FIG. 8 is a side view of the vein filter of FIG. 7;

FIG. 9 is a side view of a portion of the vein filter of FIG. 7 shown in the collapsed configuration;

FIG. 10 is a perspective view of another alternate embodiment of the vein filter of the present invention shown in the expanded configuration;

FIG. 11A is a perspective view of yet another alternate embodiment of the vein filter of the present invention shown in the expanded configuration;

FIG. 11B is a view similar to FIG. 11A showing an alternate embodiment of the hooks;

FIG. 11C is a view similar to FIG. 11A showing another alternate embodiment of the hooks;

FIG. 11D is a view similar to FIG. 11A showing yet another alternate embodiment of the filter of the present invention;

FIG. 11E is a perspective view of the filter of FIG. 11D in the collapsed position;

FIG. 11F is an enlarged view of the retention hooks of FIG. 11D;

FIG. 11G is a perspective view of an alternate embodiment of the filter of FIG. 7 having the retention hooks of FIG. 11D;

FIG. 12A is a close up perspective view of an alternate embodiment of an end of the filter having a series of cutouts to receive a retrieval snare;

FIG. 12B is a close up perspective view of an alternate embodiment of an end of the filter having cutouts to receive a retrieval snare;

FIG. 12C is a side view of the embodiment of FIG. 12B showing a retrieval snare placed in one of the cutouts between the coils;

FIG. 13A is a close up perspective view of another alternate embodiment of an end of the filter having a hook to receive a retrieval snare;

FIG. 13B is a view similar to FIG. 13A showing another alternate embodiment of the hook to receive a retrieval snare;

FIGS. 13C and 13D are perspective and top views, respectively, of an alternate embodiment of the hook to receive a retrieval snare;

FIG. 13E is an alternate embodiment of the hook of FIG. 13C;

FIGS. 13F and 13G are perspective and side views, respectively, of another alternate embodiment of the hook to receive a retrieval snare;

FIGS. 13H-13J are side views showing the method steps for engaging the hook of FIG. 13F for removing the filter utilizing a retrieval snare when the snare approaches from one orientation;

FIGS. 13K-13N are side views showing the method steps for engaging the hook of FIG. 13F for removing the filter utilizing a retrieval snare when the snare approaches from an orientation opposite the orientation of FIG. 13H;

FIGS. 14, 15 and 16 illustrate delivery and placement of the vessel filter of FIG. 1 in the inferior vena cava wherein FIG. 14 illustrates initial insertion of the delivery sheath through the femoral vein, FIG. 15 illustrates the delivery sheath being advanced toward the inferior vena cava just below (upstream) the juncture of the renal arteries; and FIG. 16 illustrates the delivery sheath fully withdrawn to place the filter in the expanded placement configuration in the inferior vena cava;

FIG. 17 is a perspective view of one embodiment of a delivery system for the vein filter;

FIG. 19 is a cross-sectional view showing the engagement of the interlocking rails of the cartridge with the hub.

DETAILED DESCRIPTION OF PREFERRED EMBODIMENTS

Figure 11H:
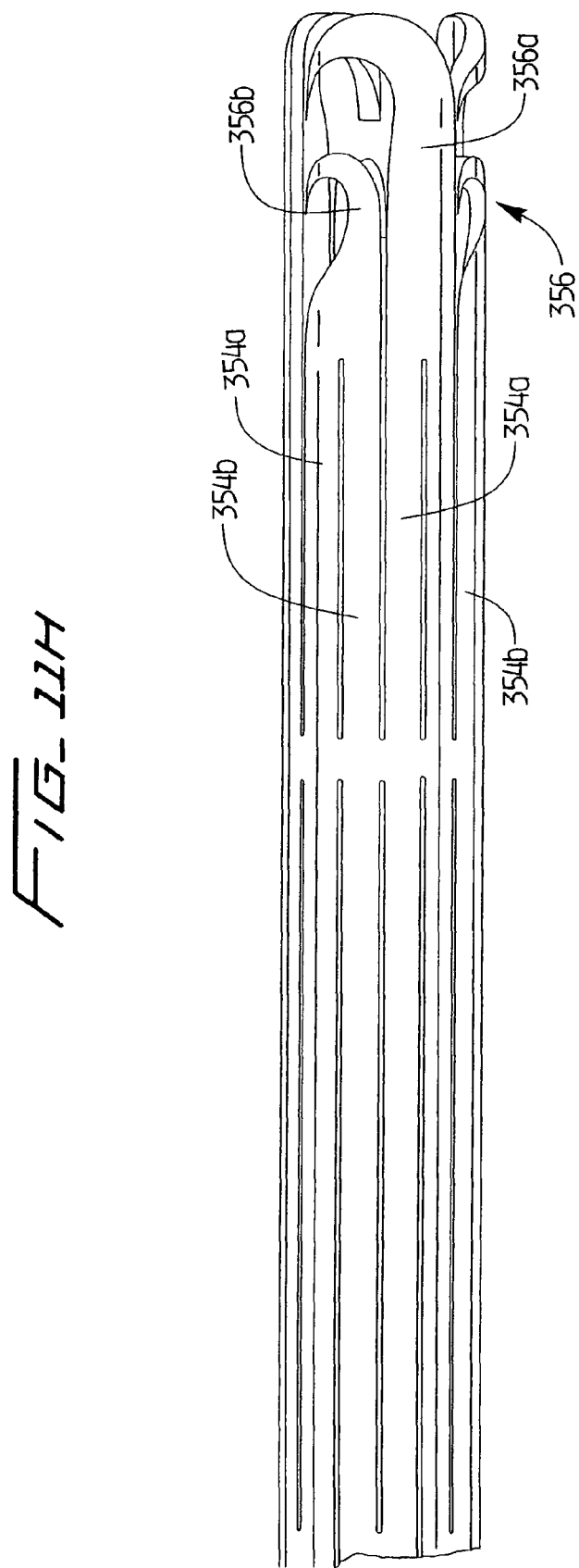
FIG. 11H is an enlarged view of the retention hooks of FIG. 11G in the collapsed position.

Turning now to the drawings, wherein like reference numerals identify similar or like components throughout the several views, the vein filter of the present invention is described for placement within the inferior vena cava to capture blood clots or other particles which could otherwise pass to the lungs.

The filter is movable from a low profile collapsed configuration to facilitate insertion through the delivery sheath to a larger expanded placement configuration to enable atraumatic engagement with the vessel walls to secure (mount) the filter within the inferior vena cava. The filter is substantially bell-shaped and has a flared region (portion/section) and a filtering region (portion/section). As described in more detail below, the filtering portion has inwardly directed struts, terminating in a converging region, thereby directing particles toward the central axis of the filter. By directing the particles to the center, they will be exposed to greater blood flow which improves dissolution of the particles. The other portion increases in transverse dimension to form a flared region. The flare provides less contact area than a straight region, resulting in less tissue ingrowth to facilitate removal of the filter if desired. The flare also reduces the chance of vessel distortion if inserted into a curved vena cava.

Turning now to details of the filter of the present invention and with initial reference to FIGS. 1 and 2, the filter is designated generally by reference numeral 10 and is shown in a collapsed configuration for delivery. Filter 10 is preferably formed from a single tube 11. In a preferred embodiment, the filter 10 is composed of shape memory material, such as Nitinol, a nickel titanium alloy, or elgiloy however, other materials such as stainless steel are also contemplated. A plurality of cutouts 12 are formed in the filter 10, preferably by laser cutting although other techniques are contemplated. In the illustrated embodiment, six elongated cutouts are formed, creating six strips or struts 14 of substantially uniform width separated by the cutouts 12 and extending from tubular portion 18.

The collapsed configuration of filter 10 reduces the overall profile to facilitate delivery to the site. The diameter of filter 10 in the collapsed configuration is represented by reference D1 and preferably is about 2 mm and more preferably about 1.7 mm. Other dimensions are also contemplated. The diameter or transverse dimensions of the filter in the expanded placement configurations (e.g. FIGS. 4A and 5) is greater than the diameter or transverse dimension D1 in the collapsed (delivery) configuration. The filter is thus preferably dimensioned for insertion through a 6 French delivery system and through a 6 French catheter.

FIGS. 3-5 illustrate the expanded placement configuration of the filter 10. Filter 10 is generally bell-shaped in configuration. Filter 10 has a flared region 17 and a converging region 21 at the filtering section 19. In larger vessels, the filter can expand to a diameter D2 shown in FIG. 5. In smaller vessels, the filter expands to a smaller diameter, e.g. D3, shown in FIG. 4. Diameters (or transverse dimensions) D2-D3 preferably range from about 18 mm to about 32 mm, depending on the internal diameter of the vessel wall as will be explained in more detail below. Other dimensions are also contemplated.

The elongated struts 14 are spaced apart as shown and extend at an angle away from the longitudinal axis L of filter 10 in region 17 to provide a flare. Preferably, this angle or taper is about 10°, although other dimensions are contemplated. In the filtering region 19, beginning at an intermediate portion of the filter (the transition between the first and second regions 17, 19) the struts 14 curve or bend inwardly (region 23) toward the longitudinal axis and then extend inwardly at an angle to the tubular portion 18, thereby forming an angle with the longitudinal axis. In the illustrated embodiment, when expanded, the six struts 14 are shown spaced approximately 60 degrees apart. It is also contemplated that a fewer or greater number of struts could be provided and spacing other than 60 degrees be provided.

In the expanded placement configuration, a portion of the each elongated strut 14 has an outer surface 20 for engagement with the vessel wall to retain the filter 10 in position in the vessel. This region is angled with respect to the longitudinal axis. The outer surface 20 of struts 14 could be roughened to enhance engagement. Alternatively, a plurality of atraumatic tabs, barbs or other penetrating members can extend from the outer surface 20 of the struts 14 to engage the vessel wall to retain the filter. FIGS. 6A and 6B show examples of such retention features. In FIG. 6B, the filter has a series of hemispherical cutouts 152 formed along the length of the struts 154 forming pointed edges 156 to engage the vessel wall. The cutouts 152 can be formed along the length of the strut 154 or alternatively be formed only along a portion of the length. The cutouts can also be formed on fewer than all the struts.

In the embodiment of FIG. 6A, the filter has anchoring elements 162 formed by cutouts 163 at the ends of the struts 164. Anchoring elements 162 have pointed ends 165. In the collapsed configuration the anchoring elements 162 and their pointed ends 165 are aligned with the struts 164, substantially parallel with the longitudinal axis of the filter to maintain a reduced profile. When the filter moves to the expanded configuration, the pointed ends 165 face outwardly as shown in FIG. 6A. Anchoring elements 162 can be placed in the end regions of the strut or in other locations. The anchoring elements can also be placed in the opposite direction shown.

In the embodiment of FIG. 11A, the struts 174 of filter 170 terminate in hooks 172 which extend substantially perpendicular from the strut. Hooks extend from the substantially V-shaped region 179 formed by the joining of connecting struts 174a, 174b. In the alternate embodiment of FIG. 11C, struts 184 of filter 180 also terminate in substantially perpendicular hooks 182, however this arrangement is achieved by torquing the connecting struts 184a, 184b at the curved region 185 so the hooks bend out of the plane. As shown, hooks 182 extend from V-shaped region 189 formed by the connecting struts 184a, 184b. In the alternate embodiment of FIG. 11B, the hooks 192 of filter 190 (having struts 194) lie in the plane of the connecting struts 194a, 194b, flush with the wide width surface "w" of the V-shaped region 199 of connecting struts 194a, 194b.

In the alternate embodiment of FIGS. 11D-11F, the hooks 302 lie in the same plane as the connecting struts 304a, 304B of struts 310 as in FIG. 11B; however the hooks of filter 301 are of two different sizes. More specifically, hooks 302a are larger than hooks 302b. Preferably when formed in a laser cut tube, hooks 302a are formed so that they occupy a region equivalent to the transverse dimension of two adjacent struts. For example, in the collapsed configuration, hook 302a occupies a region (dimension) of four connecting struts while smaller hook 302b would only occupy the region (dimension) of two connecting struts. Smaller hooks 302b are spaced axially inwardly with respect to larger hooks 302a to minimize the collapsed profile (transverse dimension) of the filter when collapsed for insertion. In this preferred embodiment, smaller hooks 302b occupy the space created by the larger hooks 302a so they can be considered as nesting within larger hooks 306a. Stated another way, each hook 302b has an outer surface 307 which conforms (follows the contour) to an inner surface 309 of a hook 306a. The penetrating tips 306a, 306b in hooks 302a, 302b, respectively, penetrate the tissue to retain the filter, preferably temporarily.

The aforedescribed hooks 172, 182, 192, 302 can be used with any of the disclosed embodiments (see e.g. FIG. 11G). Such hooks can also be formed or placed on fewer than all the struts.

Referring back to FIGS. 3-5, the filter portion of filter 10 will now be discussed. As noted above, the filtering section of filter 10 at a first end of the filter is designated generally by reference numeral 19 and includes the converging region 21. Filtering section 19 extends from the flared region 17, and extends toward the central longitudinal axis L of the filter 10 and converges at portion 32 into tubular portion 18. At the transition region between the filtering and flared regions 19, 17, struts 14 bend inwardly (region 23), then extend radially inwardly toward the tubular portion 18, and transition to the tubular portion 18. The tubular portion 18 and converging region 19 of the filter 10 are spaced both axially outwardly and radially inwardly from the bend regions 23 of the strut 14. (Axially outwardly is represented by arrow "a" and radially inwardly is represented by arrow "b" in FIG. 4A). The filter is designed to direct particles to the center of the filter and vessel. (Trapping the particles at the center rather than the edges of the filter is more desirable because there is less blood flow at the edges of the vessel and greater blood flow at the center to better dissolve the particles.) For clarity, not all of these sections of each strut 14 are labeled in the drawings, it being understood that the non-labeled struts can have the same configurations.

Turning now to the flared region 17, each strut 14 is divided into two connecting strut portions 14a, 14b. Preferably, each strut portion 14a, 14b is about one half the width of the undivided strut 14, although other widths are contemplated. The strut portions 14a, 14b of each divided strut 14 extend in opposite directions and include a curved region 25 as the strut portions 14a, 14b each extend toward respective strut portion 14a or 14b of an adjacent strut. That is, strut portions 14a, 14b form connecting portions to connect adjacent struts 14 as connecting strut 14a of one strut is connected to connecting strut 14b of an adjacent strut. Connecting strut portion 14a on one strut and portion 14b of another strut converge at end region 29 of the filter and form a substantially V-shaped region. Six such V-shaped end portions are preferably formed, each portion connecting adjacent struts. Note that although all six struts 14 are shown interconnected, it is also contemplated that fewer than all the struts can be interconnected.

It should be understood that the elongated struts 14 bend as they move from their collapsed position to their expanded placement configuration. Their designations of longitudinal, angled, curved, bowed, connected, connecting strut, etc. in the illustrated embodiments refer to the same integral strut and are divided into such regions for ease of understanding. Therefore, stated another away, the filter 10 can be viewed as having a filtering section 19 at a first end extending from the tubular portion 18. As viewed, each of the struts 14 emerges from the tubular portion 18 at an angle that extends outwardly away from the center to transition to curved portions 23. The curved portions 23 extend outwardly away from the longitudinal axis forming a flare or region of progressively increasing transverse dimension. In this flared region 17, near a second end of the filter (opposite the end containing tubular portion 18), the struts 14 are interconnected by connecting struts 14a, 14b that curve inwardly toward the connecting strut 14a or 14b of an adjacent strut to form a substantially V-shaped end portion.

In the placement (expanded) configuration, the filter 10 moves towards its memorized position and the extent it returns to its fully memorized position will be dependent on the size of the vessel in which the filter 10 is inserted. (The larger the vessel, the closer the filter comes to returning to its fully memorized position). This can be understood by comparing FIGS. 4A and 5 which illustrate by way of example two possible expanded dimensions of the filter; FIG. 4A showing expansion to a smaller dimension occurring in smaller diameter vessels and FIG. 5 showing expansion to a larger dimension occurring in larger diameter vessels.

To enable movement between an expanded and collapsed configuration, the filter tube of the embodiments described herein is preferably made of shape memory metal material, such as Nitinol, a nickel titanium alloy. The memorized configuration of the filter 10 is shown in FIG. 1. To facilitate passage of the filter 10 through the lumen of the delivery sheath 100 (shown in FIG. 14 in conjunction with the method of insertion) and into the vessel, cold saline is injected into the delivery sheath or catheter 100 and around the filter 10 in its collapsed position within the delivery sheath 100. This shape memory material characteristically exhibits rigidity in the austenitic state and more flexibility in the martensitic state. The cold saline maintains the temperature dependent filter 10 in a relatively softer condition as it is in the martensitic state within the sheath. This facilitates the exit of filter 10 from the sheath 100 as frictional contact between the filter 10 and the inner surface of the sheath would otherwise occur if the filter was maintained in a rigid, i.e. austenitic, condition.

Once ejected from the delivery sheath or catheter 100, the filter is no longer cooled and is exposed to the warmer body temperature, which causes the filter 10 to return towards its austenitic memorized configuration.

The filter 10 (and other filters described herein) can be inserted through the jugular vein in the neck of the patient or through the femoral vein in the leg of the patient or the arm. The filters can also be placed in the superior vena cava.

FIGS. 14-16 illustrate delivery and placement of the filter 10, by way of example, in the inferior vena cava. Delivery catheter 100 is inserted through the femoral vein "f" and advanced through the iliac arteries into the inferior vena cava. Delivery catheter would be withdrawn once the tip of the sheath is adjacent the structure so that withdrawal of the sheath would place the filter in the desired location of FIG. 16. Tubing 104 and valve assembly 106 enable saline injection. Delivery catheter 100 is withdrawn to enable filter 10 to be warmed by body temperature to transition to the expanded placement configuration. The other filters described herein could be inserted in the same manner. Note it is implanted in the orientation such that filter section 19 is downstream of the flared section 17. This enables blood clots or other particles to be directed to the center of the filter section by the angled struts. Thus the direction of insertion, e.g. upstream or downstream direction, will determine how the filter is to be positioned in the delivery catheter.

In an alternate embodiment of the filter, the strut width can vary. For example, the struts can be wider at the flared region than at the filtering portion. This is preferably achieved by removing material to create the thinner portions. These thinner portions increase the flexibility of the filter for forming the angled and curved portions upon deployment. Alternatively, the filter can have struts which are thinner, rather than wider, at the flared region, than at the angled and curved regions of the filtering portion. This would provide more stability at the curved regions. The adjustment of the widths is designed to strike a balance between stability and flexibility of the various regions of the filter. Thus, other width variations are contemplated such as making multiple width changes within each strut and/or in different struts.

FIGS. 7-9 illustrate an alternate embodiment of the filter, designated by reference numeral 110. Filter 110 is similar to filter 10 except for end region 121. That is, like filter 10, filter 110 has a filtering region 119 which extends from the flared region 117, and extends toward the central longitudinal axis L of the filter 110 and converges at portion 132 into tubular portion 118. Struts 114 bend inwardly toward the longitudinal axis of the filter 10 at region 123. For clarity, not all of these sections of each strut 114 are labeled in the drawing, it being understood that the non-labeled struts can have the same configurations. The flared region 117 as in filter 10 is of an angle preferably about 8 degrees although other angles are contemplated.

The end region 121 of filter 110 where the struts 114 interconnect differs from filter 10. In filter 110, the struts 114 are interconnected by connecting strut portions 114*a*, 114*b* that curve outwardly away from the central axis and then inwardly toward each other to form a substantially V-shaped end portion 127. At the outward curved or bowed portion 124, the connecting struts are joined to connecting struts of adjacent struts 114 (region 125). Thus, a closed geometric shape 133 is formed as shown. The closed shape as shown is substantially oval in configuration, although other shapes are contemplated. Six such closed geometric shapes are preferably formed, each connecting adjacent struts, although fewer closed shapes are contemplated if fewer than all the struts are interconnected. Also, the length of the region 125 where the struts are joined can be shorter or longer than that shown, thereby changing the configuration of the closed geometric shape (e.g. making it longer or shorter).

Stated in other words, each strut 114 divides into two connecting strut portions 114*a*, 114*b* which initially extend outwardly from each other. As each strut extends outwardly, the strut portion 114*a* joins the strut portion 114*b* of an adjacent strut at region 125. After this joined region 125, the strut portions 114*a* and 114*b* which emanate from the same strut extend inwardly towards each other and are joined at their ends into a substantially V-shaped end, designated by reference numeral 127.

The collapsed configuration of filter 110 is shown in FIG. 9 with cutouts 112 forming six struts 114. Regions 113 illustrate where struts 114 divide.

In the alternate embodiment of FIG. 10, filter 150 resembles filter 10 of FIG. 1 except for the additional connecting struts or ribs 152. These ribs increase the stability of the filter 150. As shown, the two ribs 152 extend from adjacent struts 154 and curve inwardly towards each other and are joined at region 156 (forming a V-like connection). The ribs 152 can be arranged so they are axially aligned as in FIG. 10 or alternatively can be staggered, i.e. spaced axially (not shown). Also, the ribs can be placed between fewer than all the struts and the ribs can be utilized with any of the foregoing embodiments. Note that the ribs are preferably integrally formed with the filter, formed by the laser cutting process mentioned above; however, alternatively the ribs can be attached to the struts. Struts 154 divide into connecting struts 154*a*, 154*b* in the embodiment of FIG. 1.

FIGS. 11G and 11H illustrate an alternate embodiment of the filter of FIG. 7 having the hooks of filter 301 of FIG. 11D. Filter 350, like filter 110, has struts 354 which are interconnected by connecting strut portions 354*a*, 354*b* that curve outwardly then inwardly toward each other to form V-shaped portions 357, terminating in hooks 356. As in FIG. 11D, large hooks 356*a* alternate with axially offset smaller hooks 356*b* and are identical to hooks 306*a*, 306*b* of FIG. 11D.

In another embodiment, the ribs could curve radially outward near their tips, thus contacting the vessel wall and acting as a retaining mechanism.

The foregoing filters can be inserted through the femoral vein or alternatively through the internal jugular vein. It can be removed from access through the internal jugular vein or femoral vein. Various methods can be used to remove the filter such as those described in commonly assigned co-pending application Ser. No. 09/911,097, filed Jul. 23, 2001, now published application 2002-0193827-A1, published Dec. 19, 2001, the entire contents of which is incorporated herein by reference, including for example, slotted hooks, graspers, etc. A recess or cutout can also be provided at the tubular end portions to receive a snare or other device for removal. A hook 222 at tubular portion 220 is illustrated in the embodiment of FIG. 13A and is configured to receive a snare. FIG. 13B illustrates another embodiment of a hook. Hook 232 formed in tubular portion 230 forms a cutout 234 for receiving a snare or other removal device. The snare can surround and grasp both ears 235. However, the gap 237 between the ears 235 also enables a retrieval snare to lie in the gap 237 to surround and grasp one of the two ears 235.

In the alternate embodiment of FIGS. 13C and 13D, hook 272 is similar to hook 232 of FIG. 13B in that it has two ears 275 with a gap 277 therebetween. However it differs in that it has a bottom cutout 278 formed between walls 279. It also differs in that surfaces 274 of ears 275 are rounded and outer proximal walls 278a angle outwardly (proximally) to curved peak 276 then angle inwardly (wall 278b) to provide a smoother transition into the retrieval sheath. Thus, two angled transitions are provided.

In the alternate embodiment of FIG. 13E, to further enhance the transition to facilitate withdrawal into the retrieval sheath, the side walls 284 extending into ears 285 of hook 282 angle inwardly toward the longitudinal axis. Consequently, there are three angled transitions: 1) an angled transition in a first direction formed by angled walls 288a which angle proximally outwardly from the edge 285a of ears 285 to the curved peak 285b (the proximal end of the hook is designated generally by reference numeral 283); 2) an angled transition in a second direction formed by angled walls 288b which angle distally outwardly from curved peak 285b; and 3) an angled transition formed by walls 284 which angle proximally inwardly as walls 284 come closer together toward the proximal end. This results in a smoother transition into the retrieval sheath as it reduces the likelihood of the filter proximal end, i.e. the hook, being caught on the edge of the sheath—the angled edges which create camming surface for all approaches of the filter (360 degree range) will help the hook edges slide into the sheath.

FIGS. 13F and 13G illustrate another alternate embodiment of the retrieval hook of the present invention. This is the retrieval hook shown in conjunction with filter 301 of the embodiment of FIGS. 11D and 11G. Hook 290 has a curved hook 292 at the proximalmost end. This hook 292 is configured to receive a retrieval snare or other retrieval device. A portion of the wall of the hook 290 is cut out to expose the annular interior surface 294. That is, being formed from a laser cut tube, a wall portion is removed to expose curved inner wall surface 294. This annular interior surface 294 extends from radiused region 295 to proximalmost edge 296. The interior surface 294, for ease of explanation, can be considered to have an interior surface 294a at the radiused region 295 and an interior surface 295b at the hook 292. The interior surface 294b accommodates a portion of a tubular snare sheath. That is, the outer wall of the snare sheath (tube) can partially fit within the cut out region 293. This enhances removal as the snare pulls the filter hook into collinear arrangement with the sheath tube. This can be appreciated by reference to FIGS. 13H-13J discussed below. The radiused region 295, spaced axially (distal) from the hook 292, includes a radiused or curved edge defined by radiused side walls 297a, 297c and top wall 297b. The angled side walls 297a, 297c form camming surfaces to direct the hook 290 and filter into the retrieval sheath. This can be appreciated by reference to FIGS. 13K-13N discussed below.

It should be appreciated, that the hook can be formed in other ways to provide an interior annular surface to function in a similar manner as surface 294, i.e. to receive the snare tube.

It should be appreciated that any of the retrieval hooks can be used with any of the filters described herein.

In FIGS. 13H-13J, the snare approaches the retrieval hook 290 in the orientation shown. This results in a collinear arrangement. More specifically, the snare 502 is part of a retrieval system which includes a snare sheath or tube 504 through which the snare 502 extends. The distal wall 503 of snare sheath 504 provides for cinching of the snare 502. The snare sheath 504 is inserted through retrieval sheath 510. When the filter is pulled into the retrieval sheath 510 it is collapsed for removal. As discussed above, preferably cold saline is injected during the removal process to cool the sheath to transition to a softer martensitic state to facilitate removal.

In the orientation shown, as snare 502 retracts the filter, the snare sheath 504 fits into the cut out region 293 as its outer wall conforms to the inner wall surface 294b of hook 292. Thus, the hook 290 and snare sheath 504 become substantially collinear as shown in FIG. 13I. This collinear arrangement facilitates retraction into the retrieval sheath 510 as it reduces the likelihood of a wall of the hook getting caught on the distal edge 512 of the retrieval sheath 510, thus providing a smoother transition into the sheath as shown in FIG. 13J.

FIGS. 13K-13N illustrate the retrieval steps when the snare approaches from the opposite orientation of FIG. 13H, i.e. below the hook as viewed in the orientation of FIG. 13K. As the snare 502 retracts the filter towards the sheath 510, the wall 297b contacts the edge 512 of retrieval sheath 510 and due to the radiused walls 297a, 297c (depending on the side of contact), the hook is cammed downwardly (in the orientation of FIG. 13M) into the retrieval sheath 510 as shown in FIG. 13N. This provides a smooth transition into the retrieval sheath 510 as it reduces the likelihood of the hook being caught on the sheath edge.

FIG. 12A illustrates another embodiment having a series of recesses 210 along the length of the tubular portion 212. This enables the tubular portion 212 to be grasped at several locations along its length, facilitating grasping of the filter for removal. These multiple recesses or cutouts 210 are axially spaced as shown. In the embodiment of FIG. 12B, the end of the tubular portion 240 has a series of axially spaced cutouts 242 which form a coil-like engagement structure. This engagement structure provides multiple engagement areas for a retrieval (removal) device, such as a retrieval snare, for grasping the filter as the device can for instance be cinched in any of the spaces (formed by the cutouts) between the turns 246 in the helical coil. FIG. 12C shows a snare 300 placed in one of the cutouts 242.

To facilitate removal of the filter from the vessel, cold saline can be injected onto the implanted filter to change the temperature of the filter to move it to a relatively softer condition to facilitate the filter being drawn in to the retrieval sheath. That is, injection of cold saline will cause the filter to approach its martensitic state, bringing the filter to a more flexible condition. The flexible condition facilitates the collapse and withdrawal of the filter into the retrieval sheath, by decreasing the frictional contact between the filter and the inner surface of the retrieval sheath.

Figure 18:
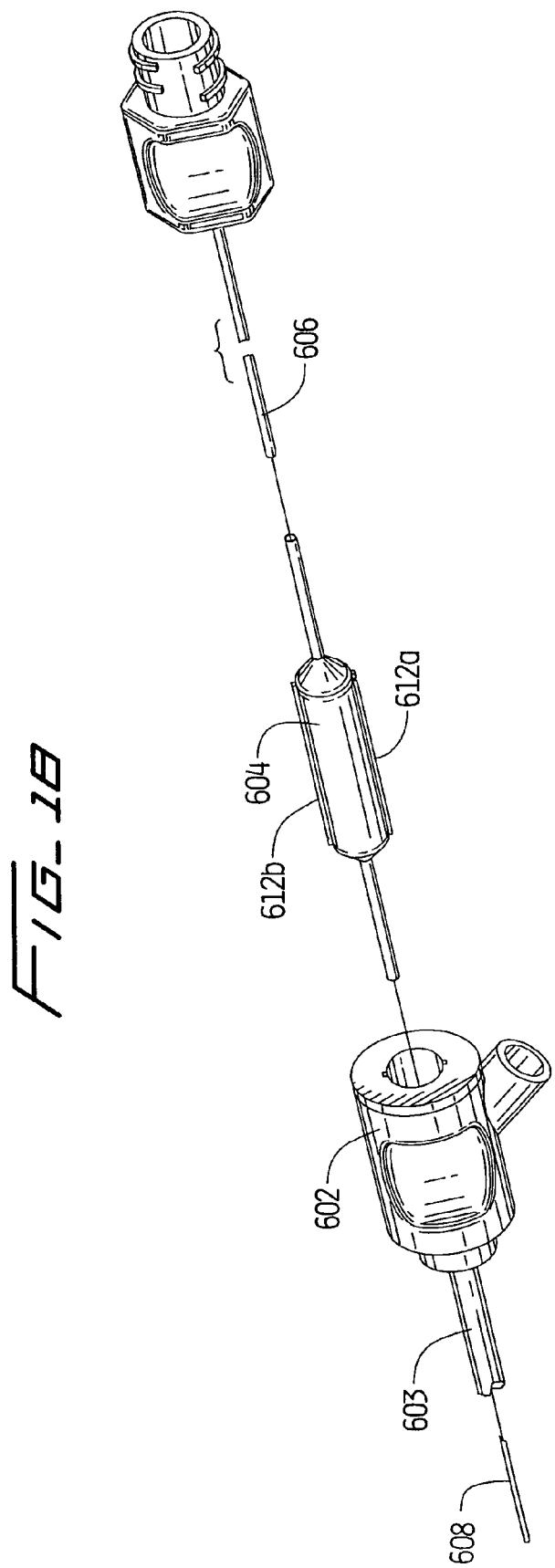
FIG. 18 is an exploded view of the delivery system of FIG. 17.

A delivery system for the filter of the present invention is shown in FIGS. 17 and 18. The delivery system 600 includes a hub 602, a cartridge 604 containing the filter, a pusher 606 and a wire 608 extending through the pusher 606. The wire 608 extends through the cartridge 604 and through the length of tube 603 to maintain a separation of the hooks, e.g. hooks 402 of filter 350 of FIG. 11G, during insertion of the delivery system and delivery of the filter. The cartridge 604 is removably attached to the hub 602, preferably by a snap-fit although other modes of attachment are also contemplated. The cartridge preferably has markings (not shown) on the outer surface to indicate a femoral or jugular direction so the user knows the orientation to attach the cartridge 604 to hub 602.

Once attached, advancement of the pusher 604 advances the filter from the cartridge and through tube 603 as the distal edge of the pusher 604 abuts the proximal end of the filter, with the wire 608 (e.g., a Nitinol wire) preventing entanglement of the retention hooks. The wire 608 also provides support (stability) for the pusher 604 as the pusher 604 is advanced over the wire 608. The filter is forced out of the distal end of the tube, where it is no longer cooled by saline and is warmed by body temperature to return toward its memorized configuration.

To enhance the retention of the cartridge 604 in the hub 602, a locking mechanism can be provided such as the mechanism of FIG. 19. The cartridge 604 has a pair of locking rails 612a, 612b, each including a respective recess 614a, 614b. The hub 602 contains a detent 620 as shown. When the cartridge 604 is inserted into the hub 602, the recess 614a of the locking rails 612a is retained by the detent 620. This locks the cartridge 604 to the hub 602 during use, preventing unwanted separation of the cartridge 604 from the hub 602. If access via the jugular artery instead of the femoral artery is desired, then the cartridge is inserted so that recess 614b of rail 612b engages detent 620 of hub 602.

While the above description contains many specifics, those specifics should not be construed as limitations on the scope of the disclosure, but merely as exemplifications of preferred embodiments thereof. For example, the filters can be inserted in other regions of the body. Also, any of the aforedescribed filters can have mounting sections of varying thickness. The foregoing filters can be made of materials other than shape memory material. Those skilled in the art will envision many other possible variations that are within the scope and spirit of the disclosure as defined by the claims appended hereto.

What is claimed is:

1. A vessel filter comprising first and second end portions, a first proximal region at the first end portion and a second region at the second end portion, the first region including a filtering section for capturing particles and having a first transverse dimension at a first terminal end of the filter, the second region including a mounting section a second terminal distal end of the filter for mounting the filter within a vessel, the mounting section having a second transverse dimension at the second terminal end of the filter, the second dimension being greater than the first transverse dimension and including vessel engaging structure to retain the filter, the first region further including a cut tubular retrieval region, the retrieval region having only one hook having a cutout exposing an internal annular surface, the hook having a single ear and having a gap configured to receive a retrieval snare of a retrieval device, the annular surface extending proximal of the gap and dimensioned to receive therein a curved outer wall of a retrieval sheath of the retrieval device.

2. The vessel filter of claim 1, wherein the retrieval region includes a radiused region having first and second curved surfaces extending distally inwardly.

3. The vessel filter of claim 1, wherein the filter is formed from a laser cut tube, the tube cut to form struts in the first and second regions.

4. The vessel filter of claim 3, wherein the hook is formed by a portion of a wall of the tube cut to expose an annular interior surface.

5. The vessel filter of claim 4, wherein a proximalmost end portion of the hook is removed to provide a surface for abutment of a retrieval sheath.

6. The vessel filter of claim 1, wherein the hook is formed radially spaced from a central longitudinal axis of the filter.

7. The vessel filter of claim 1, wherein the retrieval region includes first and second angled side walls forming camming surfaces to direct the hook and filter into a retrieval sheath.

8. The vessel filter of claim 1, further comprising a first angled wall spaced distally of the gap forming a first camming surface.

9. The vessel filter of claim 8, further comprising a second angled wall spaced distally of the gap forming a second camming surface.

10. The vessel filter of claim 9, wherein the first and second angled walls are on opposing sides of the retrieval region and an outer wall portion joins the first and second angled walls.

11. A vessel filter comprising a first distal region and a second region, the first region including a filtering section for capturing particles and having a first transverse dimension, the second region including a mounting section for mounting the filter within a vessel, the mounting section having a second transverse dimension greater than the first transverse dimension and including vessel engaging structure to retain the filter, the first region further including a cut tubular retrieval region having a longitudinal axis, the retrieval region including only one hook, the hook positioned on only one side of the longitudinal axis at a proximal end thereof and a curved wall spaced axially distally from the hook to provide a caroming surface to facilitate entry into a retrieval sheath, the hook having an inner surface exposed and dimensioned to receive a portion of a retrieval device.

12. The vessel filter of claim 11, further comprising vessel engaging hooks, the vessel engaging hooks extending from the mounting section to be positioned at a terminal end of the filter.

13. The vessel filter of claim 11, wherein a proximalmost end portion of the hook is curved in a direction radially with respect to a central longitudinal axis of the filter.

14. The vessel filter of claim 11, wherein the filter is formed from a laser cut tube, the tube cut to form struts in the first and second regions.

15. The vessel filter of claim 14, wherein the hook is formed by a portion of a wall of the tube cut to expose an annular interior surface.

16. The vessel filter of claim 15, wherein a proximalmost end portion of the hook is removed to provide a surface for abutment of a retrieval sheath.

17. The vessel filter of claim 11, wherein the cut tubular region at the camming surface has a transverse dimension greater than a transverse dimension of the cut tubular region at the hook.

18. The vessel filter of claim 11, wherein the retrieval region further includes a second curved wall on an opposing side of the retrieval region forming a second camming surface engageable with a portion of the retrieval sheath.

* * * * *